(12) United States Patent
Matsuno et al.

(10) Patent No.: US 9,678,259 B2
(45) Date of Patent: Jun. 13, 2017

(54) OPTICAL FILTER DEVICE AND MANUFACTURING METHOD FOR THE OPTICAL FILTER DEVICE

(71) Applicant: Seiko Epson Corporation, Tokyo (JP)

(72) Inventors: Yasushi Matsuno, Matsumoto (JP); Akira Sano, Shiojiri (JP)

(73) Assignee: Seiko Epson Corporation (JP)

( * ) Notice: Subject to any disclaimer, the term of this patent is extended or adjusted under 35 U.S.C. 154(b) by 522 days.

(21) Appl. No.: 13/766,122

(22) Filed: Feb. 13, 2013

(65) Prior Publication Data

US 2013/0208359 A1    Aug. 15, 2013

(30) Foreign Application Priority Data

Feb. 14, 2012 (JP) ................................. 2012-029864

(51) Int. Cl.
| | |
|---|---|
| G02B 5/28 | (2006.01) |
| G02B 26/00 | (2006.01) |
| G01N 21/65 | (2006.01) |
| G01J 3/28 | (2006.01) |
| G01J 3/42 | (2006.01) |
| G01J 3/44 | (2006.01) |

(Continued)

(52) U.S. Cl.
CPC ............ *G02B 5/284* (2013.01); *G01J 3/2823* (2013.01); *G01J 3/42* (2013.01); *G01J 3/44* (2013.01); *G01J 3/50* (2013.01); *G01J 3/51* (2013.01); *G01N 21/65* (2013.01); *G02B 26/001* (2013.01); *G01J 2003/1234* (2013.01); *G01J 2003/2826* (2013.01); *Y10T 29/49904* (2015.01)

(58) Field of Classification Search
CPC ........ G02B 26/001; G02B 5/28; G02B 5/284; G02B 27/0006; G02B 6/29358; G02B 6/29395; G02B 5/201; G02B 5/285; G02B 1/005; G02B 1/14; G02B 1/16; G02B 26/007; G02B 26/02; G02B 26/06; G02B 7/006; G02B 13/22; G02B 1/11
USPC ................ 359/557, 578, 579, 260, 261, 263
See application file for complete search history.

(56) References Cited

U.S. PATENT DOCUMENTS

| | | |
|---|---|---|
| 5,035,495 A | 7/1991 | Toyoda et al. |
| 5,877,903 A | 3/1999 | Adachi |

(Continued)

FOREIGN PATENT DOCUMENTS

| | | |
|---|---|---|
| JP | 62-154680 | 7/1987 |
| JP | 63-210912 A | 9/1988 |

(Continued)

*Primary Examiner* — Scott J Sugarman
*Assistant Examiner* — Sharrief Broome
(74) *Attorney, Agent, or Firm* — Harness, Dickey & Pierce, P.L.C.

(57) ABSTRACT

An optical filter device includes an interference filter and a housing. The interference filter includes a fixed substrate, a movable substrate joined to the fixed substrate, a fixed reflective film provided on the fixed substrate, and a movable reflective film provided on the movable substrate and opposed to the fixed reflective film across an inter-reflective film gap. The housing includes a base substrate on which the interference filter is arranged. A fixing member is arranged between the movable substrate and the base substrate. The movable substrate is fixed to the base substrate by the fixing member in one place excluding a region where the movable reflective film is provided.

19 Claims, 17 Drawing Sheets

(51) Int. Cl.
*G01J 3/50* (2006.01)
*G01J 3/51* (2006.01)
*G01J 3/12* (2006.01)

(56) References Cited

U.S. PATENT DOCUMENTS

| | | |
|---|---|---|
| 6,285,504 B1 * | 9/2001 | Diemeer ............... G02B 6/125 |
| | | 359/578 |
| 6,985,281 B2 | 1/2006 | Wagner et al. |
| 7,002,697 B2 | 2/2006 | Domash et al. |
| 7,514,685 B2 | 4/2009 | Yoshida |
| 2005/0057331 A1 | 3/2005 | Murata |
| 2007/0242920 A1 * | 10/2007 | Lin et al. ........................ 385/27 |
| 2009/0243006 A1 | 10/2009 | Takahashi et al. |
| 2010/0004511 A1 * | 1/2010 | Kamihara ............... G01J 3/02 |
| | | 600/160 |
| 2011/0037810 A1 | 2/2011 | Wang |
| 2011/0128549 A1 * | 6/2011 | Nishimura ............... G01J 3/26 |
| | | 356/450 |
| 2012/0235038 A1 | 9/2012 | Nishikawa et al. |

FOREIGN PATENT DOCUMENTS

| | | |
|---|---|---|
| JP | 1-312877 | 12/1989 |
| JP | 02-257676 A | 10/1990 |
| JP | 10-090576 A | 4/1998 |
| JP | 2001-223404 A | 8/2001 |
| JP | 2004-287215 A | 10/2004 |
| JP | 2005-055670 A | 3/2005 |
| JP | 2005-510756 | 4/2005 |
| JP | 2008-070163 | 3/2008 |
| JP | 2008070163 A * | 3/2008 |
| JP | 2009-260247 A | 11/2009 |
| TW | 201129790 A | 9/2011 |

* cited by examiner

OPTICAL FILTER DEVICE AND MANUFACTURING METHOD FOR THE OPTICAL FILTER DEVICE

BACKGROUND

1. Technical Field

The present invention relates to an optical filter device and a manufacturing method for the optical filter device.

2. Related Art

An interference filter in which reflective films are arranged to be opposed to each other across a predetermined gap on opposed surfaces of a pair of substrates is known. An optical filter device in which such an interference filter is housed in a housing (see, for example, JP-A-2008-70163 and JP-T-2005-510756) is also known.

An infrared gas detector (an optical filter device) described in JP-A-2008-70163 includes a package (a housing) including a tabular pedestal (base substrate) and a cylindrical cap. In the housing, a peripheral edge portion of the base substrate and a cylindrical end portion of the cap are connected by welding or bonding. A space for housing a Fabry-Perot filter (an interference filter) is provided between the base substrate and the gap. In the optical filter device, the interference filter is bonded and fixed to a detecting unit and the detecting unit is bonded and fixed on a pedestal of a can-shaped package.

JP-T-2005-510756 describes an optical filter device (a photoelectronic device) in which a tunable optical filter (an interference filter) is fixed and housed on the inside of a package (a housing). In the optical filter device, the interference filter is arranged in a vertical stack attached to the upper surface of a header (a base substrate) of the housing.

As explained above, JP-A-2008-70163 and JP-T-2005-510756 describe that the interference filter is housed and fixed on the inside of the housing but do not describe a specific method therefor.

For example, it is likely that the reflective film warps due to a difference between the coefficients of thermal expansion of the interference filter and the base substrate to which the interference filter is fixed. When the interference filter and the base substrate are fixed by an adhesive, it is likely that the reflective film warps due to contraction of the adhesive when the adhesive hardens. When the reflective film of the interference filter warps, the optical characteristics of the interference filter is affected.

SUMMARY

An advantage of some aspects of the invention is to provide an optical filter device in which warping of a reflective film of an interference filter can be suppressed and a manufacturing method for the optical filter device.

An aspect of the invention is directed to an optical filter device including: an interference filter including a first substrate, a second substrate arranged to be opposed to the first substrate and joined to the first substrate, a first reflective film provided on the first substrate, and a second reflective film provided on the second substrate and opposed to the first reflective film across an inter-reflective film gap; and a housing configured to house the interference filter. The housing includes a base substrate on which the interference filter can be arranged. A fixing member for fixing the second substrate to the base substrate is arranged between the second substrate and the base substrate. In a plan view in which the second substrate is viewed from a substrate thickness direction, the second substrate is fixed by the fixing member in one place excluding a region where the second reflective film is provided.

According to the aspect of the invention, the optical filter device includes the interference filter and the housing configured to house the interference filter. The housing includes the base substrate on which the interference filter can be arranged. In the plan view in which the second substrate is viewed from the substrate thickness direction, the second substrate of the interference filter is fixed to the base substrate by the fixing member in the place excluding the region where the second reflective film is provided. In the aspect of the invention, when a fixing place by the fixing member is one place, the fixing excludes arranging the fixing member over the entire surface between the second substrate and the base substrate and fixing the second substrate and excludes fixing the second substrate in a plurality of places dispersed from one another. For example, when the second substrate is arranged in a position opposed to the base substrate across the second reflective film in the plan view, the second substrate is fixed in a plurality of places dispersed from one another. In the aspect of the invention, when the fixing place by the fixing member is one place, the fixing includes concentratedly arranging fixing members at a plurality of points in one place and fixing the second substrate.

In the optical filter device in which the fixing member is arranged over the entire surface between the second substrate and the base substrate or arranged in the dispersed plurality of places, stress due to a difference between coefficients of thermal expansion of the second substrate and the base substrate tends to act over the entire second substrate. When an adhesive is used as an example of the fixing member, stress due to contraction caused when the adhesive is hardened tends to act on the second substrate. Since the second substrate is joined to the first substrate, the stress tends to act on the first substrate as well. When the stress acts in this way, the second reflective film of the second substrate and the first reflective film of the first substrate warp and the optical characteristics of the interference filter are affected.

On the other hand, in the optical filter device according to the aspect of the invention, as explained above, the second substrate and the base substrate are fixed in one place by the fixing member. Therefore, the stress due to the difference between the coefficients of thermal expansion and the contraction stress during the adhesive hardening less easily act on the second substrate and the first substrate. As a result, with the optical filter device, it is possible to suppress warping of the second reflective film and the first reflective film.

In the optical filter device according to the aspect of the invention, it is preferable that, in the plan view in which the second substrate is viewed from the substrate thickness direction, the second substrate is fixed in an outer peripheral portion of a surface opposed to the base substrate.

In this configuration, in the plan view in which the second substrate is viewed from the substrate thickness direction, the second substrate is fixed in the outer peripheral portion of the surface opposed to the base substrate.

Therefore, the fixing place by the fixing member can be set in a position away from the second reflective film and the first reflective film. Therefore, it is possible to further suppress warping of the second reflective film and the first reflective film by the stress due to the difference between the coefficients of thermal expansion of the members (the second substrate and the base member) and the contraction stress during the adhesive hardening.

In the optical filter device according to the aspect of the invention, it is preferable that, in the plan view in which the second substrate is viewed from the substrate thickness direction, the second substrate is fixed at a corner portion of a surface opposed to the base substrate.

In this configuration, in the plan view in which the second substrate is viewed from the substrate thickness direction, the second substrate is fixed at the corner portion of the surface opposed to the base substrate.

Therefore, the fixing place by the fixing member can be set in a position further spaced apart from the second reflective film and the first reflective film. Therefore, it is possible to further suppress warping of the second reflective film and the first reflective film by the stress due to the difference between the coefficients of thermal expansion of the members (the second substrate and the base member) and the contraction stress during the adhesive hardening.

Another aspect of the invention is directed to an optical filter device including: an interference filter including a first substrate, a second substrate arranged to be opposed to the first substrate and joined to the first substrate, a first reflective film provided on the first substrate, and a second reflective film provided on the second substrate and opposed to the first reflective film across an inter-reflective film gap; and a housing configured to house the interference filter. The housing includes a base substrate on which the interference filter can be arranged. The second substrate includes a non-joining section not joined to the first substrate. A fixing member for fixing the second substrate to the base substrate is arranged between the non-joining section and the base substrate.

According to this aspect of the invention, the non-joining section of the second substrate is fixed to the base substrate by the fixing member. In other words, the fixing member fixes the non-joining section of the second substrate and the base substrate in a position away from a region where the first substrate and the second substrate are joined (a substrate joining region).

When the non-joining section of the second substrate and the base substrate are fixed by the fixing member in a position corresponding to the substrate joining region, the stress due to the difference between the coefficients of thermal expansion of the members and the contraction stress during the hardening of the adhesive used as the fixing member tend to act on the first substrate as well. The position corresponding to the substrate joining region refers to, in the plan view in which the second substrate is viewed from the thickness direction, a position overlapping the region where the first substrate and the second substrate are joined.

According to the aspect of the invention, the fixing place of the non-joining section and the base substrate is spaced apart from the region where the first substrate and the second substrate are jointed. Therefore, as explained above, the stress due to the difference between the coefficients of thermal expansion of the members and the contraction stress during the adhesive hardening less easily act on, in particular, the first substrate. According to the aspect of the invention, the fixing place of the non-joining section and the base substrate is spaced apart from positions where the first reflective film and the second reflective film are provided. As a result, with the optical filter device according to the aspect of the invention, it is possible to suppress warping of the first reflective film and the second reflective film. In the aspect of the invention, the non-joining section of the second substrate and the base substrate may be fixed in a plurality of places. This is because the fixing place by the fixing member can be set in a position spaced apart from the substrate joining region and the influence of the stress can be reduced compared with the influence of stress caused when the non-joining section of the second substrate and the base substrate are joined in a plurality of places in the substrate joining region. However, as explained below, even when the non-joining section and the base substrate are fixed, the fixing place is desirably one place.

In the optical filter device according to the aspect of the invention, it is preferable that the second substrate is fixed by the fixing member in one place of the non-joining section.

In this configuration, the second substrate is fixed to the base substrate in one place of the non-joining section. In other words, the fixing place is smallest one place and is spaced apart from the substrate joining region.

Therefore, as explained above, the stress due to the difference between the coefficients of thermal expansion and the contraction stress during the adhesive hardening much less easily act on the second substrate and the first substrate. Therefore, with the optical filter device according to the aspect of the invention, it is possible to more surely suppress warping of the first reflective film and the second reflective film.

In the optical filter device according to the aspect of the invention, it is preferable that, in the plan view in which the second substrate is viewed from the substrate thickness direction, the non-joining section is a projecting section where the second substrate is arranged to project further to the outer side than the first substrate.

In this configuration, the projecting section of the second substrate is the non-joining section.

Therefore, the position of the non-joining section can be set in a position more surely spaced apart from the region where the first substrate and the second substrate are joined. Therefore, as explained above, the stress due to the difference between the coefficients of thermal expansion and the contraction stress during the adhesive hardening much less easily act on the second substrate and the first substrate. Therefore, with the optical filter device according to the aspect of the invention, it is possible to more surely suppress warping of the first reflective film and the second reflective film.

In the optical filter device according to the aspect of the invention, it is preferable that the optical filter device further includes an actuator configured to bend the second substrate by applying voltage and change a gap amount of the inter-reflective film gap. The actuator includes a first electrode provided on the first substrate and a second electrode provided on the second substrate and opposed to the first electrode. A second terminal extracting section connected to the second electrode is formed in the projecting section.

In this configuration, the optical filter device further includes the actuator. Therefore, the optical filter device includes a variable wavelength interference filter. In the optical filter device including the variable wavelength interference filter, as explained above, it is possible to suppress warping of the first reflective film and the second reflective film.

The second electrode included in the actuator is connected to the second terminal extracting section. The second terminal extracting section is formed on the projecting section, which is the non-joining section.

Therefore, a region for forming the second terminal extracting portion does not need to be separately formed on the second substrate. The fixing place of the second substrate (the non-joining section) and the base substrate can be used as a forming place of the second terminal extracting section as well. Therefore, it is possible to suppress an increase in the size of the second substrate and realize a reduction in the size of the variable wavelength interference filter. Therefore, in the optical filter device including the variable wavelength interference filter, it is possible to realize a reduction in size while suppressing warping of the first reflective film and the second reflective film.

In the optical filter device according to the aspect of the invention, it is preferable that a substrate recess is formed in a position corresponding to the fixing member on a surface of the second substrate opposed to the base substrate.

In this configuration, the substrate recess is formed in the position, which corresponds to the place where the fixing member is arranged, on the surface of the second substrate opposed to the base substrate. Therefore, the position of the fixing member is regulated by the substrate recess. It is possible to more surely fix the second substrate and the base substrate in a desired place. For example, when a member having fluidity (e.g., an adhesive) is used as the fixing member, it is possible to suppress, with the substrate recess, the fixing member from oozing or sliding out of an application position.

Therefore, with the optical filter device according to the aspect of the invention, it is possible to surely arrange the fixing member in a desired place. Therefore, it is possible to improve the quality and the yield of the optical filter device.

In the optical filter device according to the aspect of the invention, it is preferable that a base recess is formed in a position corresponding to the fixing member on a surface of the base substrate opposed to the second substrate.

In this configuration, the base recess is formed in the position, which corresponds to the place where the fixing member is arranged, on the surface of the base substrate opposed to the second substrate. Therefore, the position of the fixing member is regulated by the base recess. It is possible to more surely fix the second substrate and the base substrate in a desired place. For example, in the fixing of the second substrate to the base substrate, when the fixing member is arranged on the base substrate side first, the fixing member only has to be arranged with reference to the base recess. Therefore, it is easy to position the fixing member. For example, when a member having fluidity (e.g., an adhesive) is used as the fixing member, it is possible to suppress, with the base recess, the fixing member from oozing or sliding out of an application position.

Therefore, with the optical filter device according to the aspect of the invention, it is possible to surely arrange the fixing member in a desired place. Therefore, it is possible to improve the quality and the yield of the optical filter device.

In the optical filter device according to the aspect of the invention, it is preferable that the optical filter device further includes a lid joined to the base substrate and configured to form, between the lid and the base substrate, an inner space in which the interference filter can be housed.

In this configuration, the interference filter is housed in the inner space of a housing formed by the base substrate and the lid. Therefore, it is possible to evacuate the housing inside of the optical filter device of air, reduce air resistance to the displacement of the reflective films, and suppress adhesion of charged particles floating in the air from adhering to the reflective films.

Still another aspect of the invention is directed to a manufacturing method for an optical filter device including: forming a first reflective film on a first substrate; forming a second reflective film on a second substrate; joining the first substrate and the second substrate such that the first reflective film and the second reflective film are arranged to be opposed to each other across an inter-reflective film gap and manufacturing an interference filter; arranging a fixing member on a base substrate; setting the second substrate side of the interference filter to be opposed to the base member and, in a plan view in which the second substrate is viewed from a substrate thickness direction, fixing the second substrate to the base substrate with the fixing member in one place excluding a region where the second reflective film is formed; and joining, to the base substrate, a lid configured to form, between the lid and the base substrate, an inner space in which the interference filter can be housed.

In the optical filter device manufactured by the manufacturing method according to this aspect of the invention, the base substrate and the second substrate are fixed in one place where the fixing member is arranged. With the optical filter device, the stress due to the difference between the coefficients of thermal expansion of the members and the contraction stress during hardening of the adhesive used as the fixing member less easily act on the second substrate and the first substrate. Therefore, with the optical filter device manufactured by the manufacturing method according to the aspect of the invention, it is possible to suppress warping of the second reflective film and the first reflective film.

Yet another aspect of the invention is directed to a manufacturing method for an optical filter device including: forming a first reflective film on a first substrate; forming a second reflective film on a second substrate; joining the first substrate and the second substrate such that the first reflective film and the second reflective film are arranged to be opposed to each other across an inter-reflective film gap and manufacturing an interference filter; arranging a fixing member on a base substrate; setting the second substrate side of the interference filter to be opposed to the base member and fixing the second substrate to the base substrate with the fixing member; and joining, to the base substrate, a lid configured to form, between the lid and the base substrate, an inner space in which the interference filter can be housed. In the joining the first substrate and the second substrate and manufacturing the interference filter, when the first substrate and the second substrate are joined, a non-joining section not joined to the first substrate is formed on the second substrate. In the fixing the second substrate to the base substrate, the second substrate is fixed to the non-joining section.

In the optical filter device manufactured by the manufacturing method according to this aspect of the invention, the non-joining section of the second substrate is fixed to the base substrate by the fixing member. In other words, the fixing member fixes the non-joining section of the second substrate and the base substrate in a position away from a region where the first substrate and the second substrate are joined (a substrate joining region).

Therefore, the stress due to the difference between the coefficients of thermal expansion of the members and the contraction stress during the adhesive hardening less easily act on, in particular, the first substrate. The fixing place of the non-joining section and the base substrate is spaced apart from the position where the first reflective film and the second reflective film are provided. Therefore, with the optical filter device manufactured by the manufacturing method according to the aspect of the invention, it is possible to suppress warping of the second reflective film and the first reflective film.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

A first embodiment of the invention is explained below on the basis of the accompanying drawings.

1. Configuration of an Optical Filter Device

Figure 1:
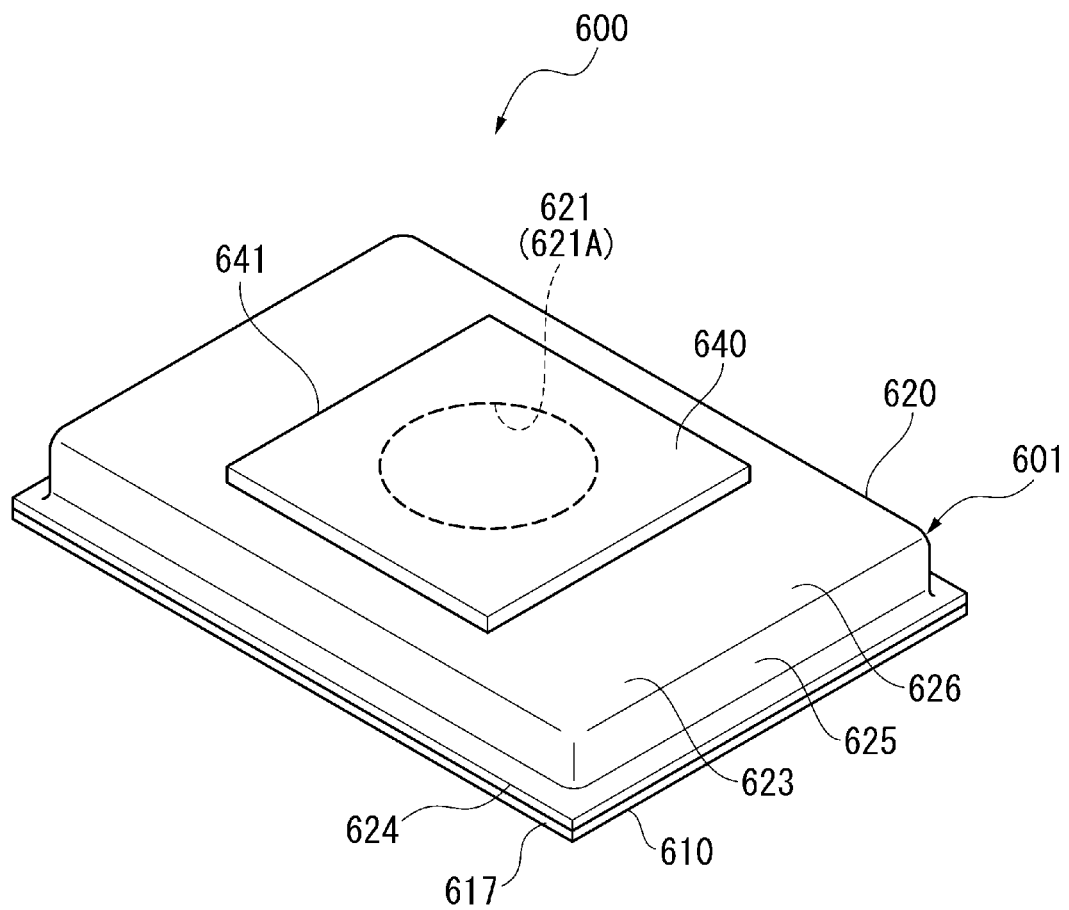
FIG. 1 is a perspective view showing a schematic configuration of an optical filter device according to a first embodiment of the invention.
Figure 2:
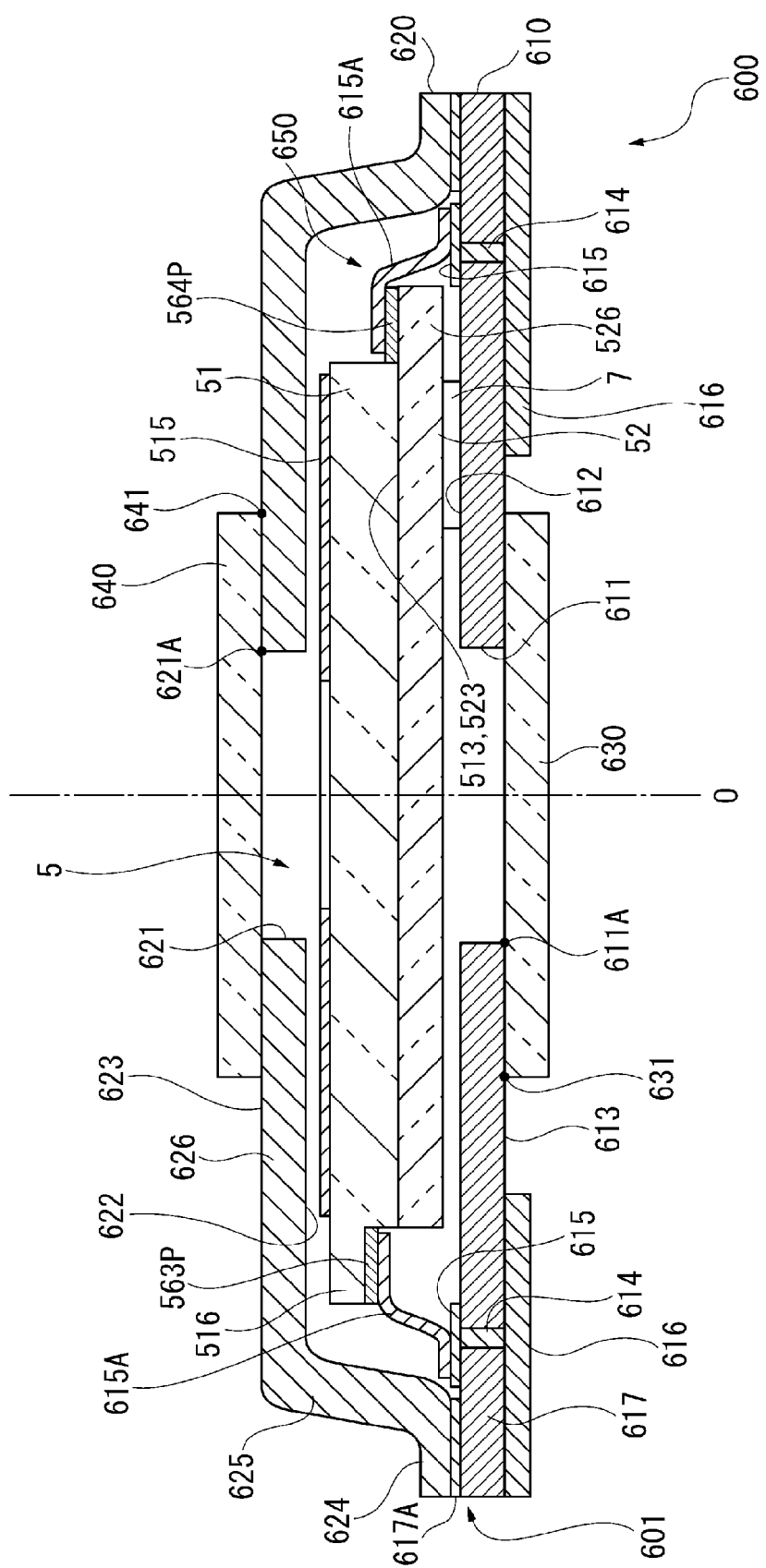
FIG. 2 is a sectional view showing a schematic configuration of the optical filter device according to the first embodiment.

FIG. 1 is a perspective view showing a schematic configuration of an optical filter device 600 according to the first embodiment of the invention. FIG. 2 is a sectional view of the optical filter device 600.

The optical filter device 600 is a device that extracts light having a predetermined target wavelength from incident test target light and emits the light. The optical filter device 600 includes a housing 601 and a variable wavelength interference filter 5 (see FIGS. 2 and 3) housed on the inside of the housing 601. The optical filter device 600 can be incorporated in an optical module such as a colorimetric sensor and an electronic apparatus such as a colorimetric apparatus or a gas analyzing apparatus. The configurations of the optical module and the electronic apparatus including the optical filter device 600 are explained in a sixth embodiment below.

2. Configuration of a Variable Wavelength Interference Filter

Figure 3:
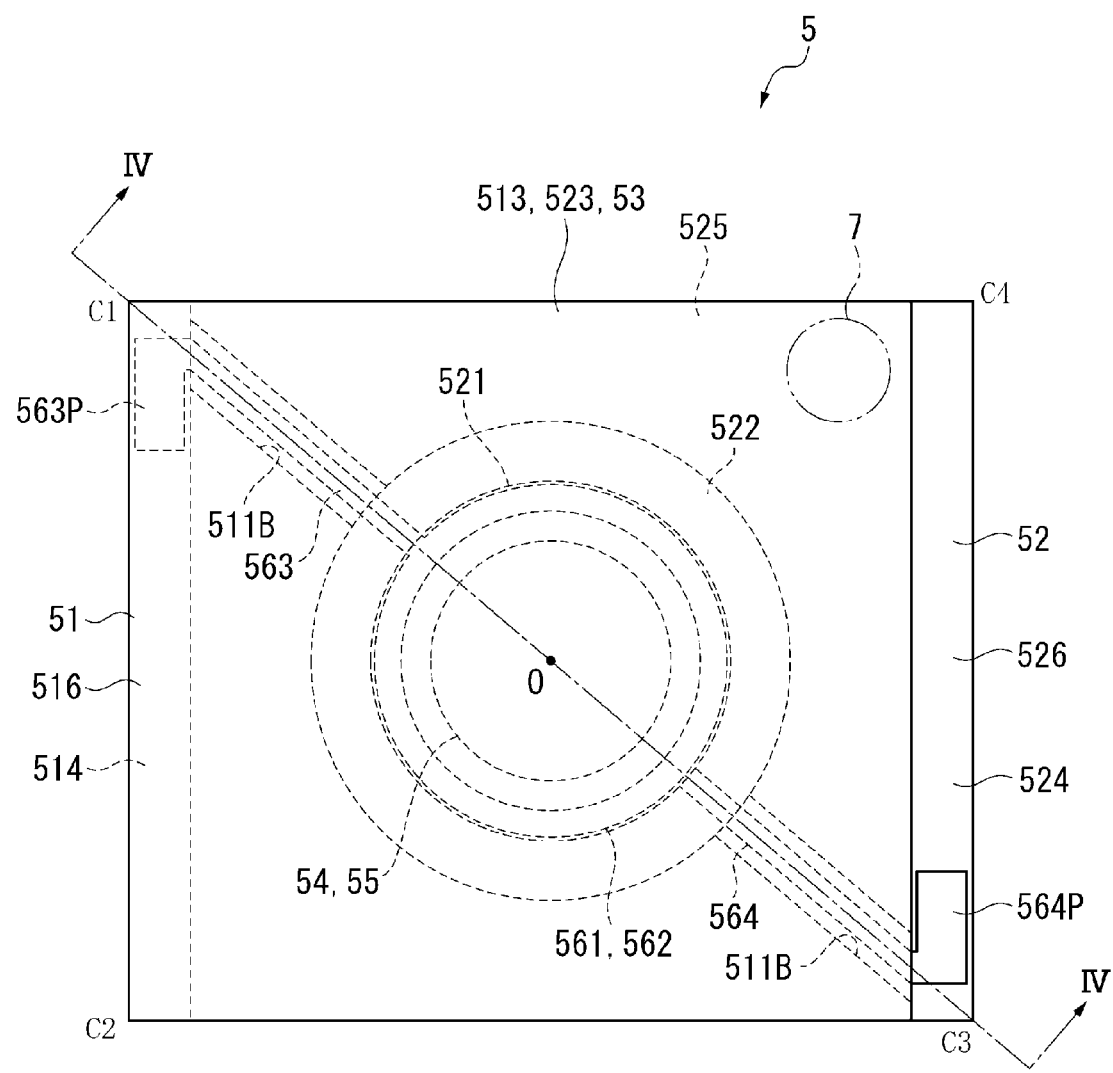
FIG. 3 is a plan view showing a schematic configuration of an interference filter housed in the optical filter device according to the first embodiment and is a diagram for explaining a positional relation between the interference filter and a fixing member.
Figure 4:
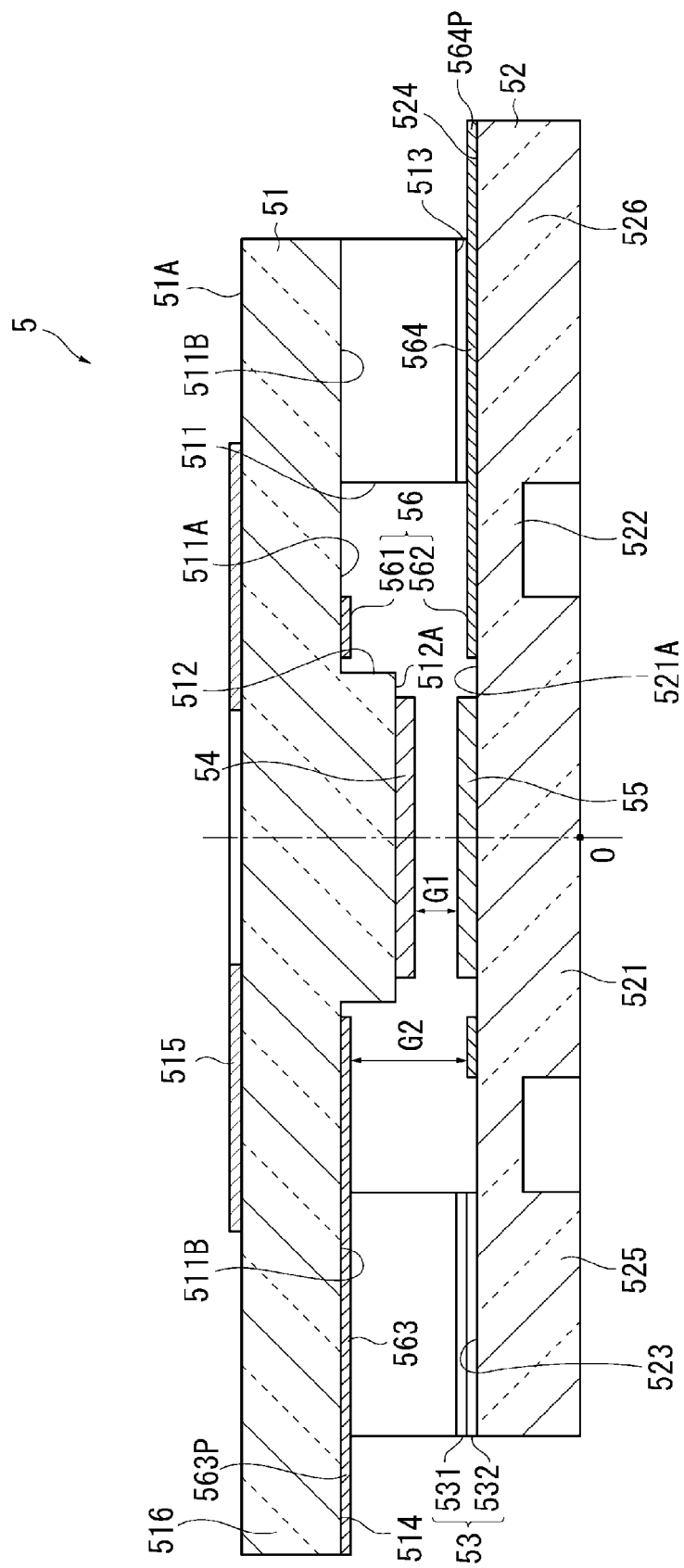
FIG. 4 is a sectional view showing a schematic configuration of the interference filter according to the first embodiment.

The variable wavelength interference filter 5 configures an interference filter according to this embodiment. FIG. 3 is a plan view showing a schematic configuration of the variable wavelength interference filter 5 provided in the optical filter device 600. FIG. 4 is a sectional view showing a schematic configuration of the variable wavelength interference filter 5 taken along a IV-IV line in FIG. 3.

As shown in FIG. 3, the variable wavelength interference filter 5 is, for example, an optical member having a rectangular tabular shape. The variable wavelength interference filter 5 includes a fixed substrate 51, which is the first substrate in the embodiment of the invention, and a movable substrate 52, which is the second substrate in the embodiment of the invention. Each of the fixed substrate 51 and the movable substrate 52 is formed of, for example, any one of various kinds of glass such as soda glass, crystalline glass, quartz glass, lead glass, potassium glass, borosilicate glass, and non-alkali glass or crystal. A first joining section 513 of the fixed substrate 51 and a second joining section 523 of the movable substrate 52 are joined by a joining film 53 (a first joining film 531 and a second joining film 532) formed of, for example, a plasma polymerization film containing siloxane as a main component, whereby the fixed substrate 51 and the movable substrate 52 are integrally formed.

In the following explanation, a plan view of the fixed substrate 51 or the movable substrate 52 viewed from a substrate thickness direction, i.e., a plan view in which the variable wavelength filter 5 is viewed from a laminating direction of the fixed substrate 51, the joining film 53, and the movable substrate 52 is referred to as the filter plan view.

On the fixed substrate 51, as shown in FIG. 4, a fixed reflective film 54 forming the first reflective film according to the embodiment of the invention is provided. On the movable substrate 52, as shown in FIG. 4, a movable reflective film forming the second reflective film according to the embodiment of the invention is provided. The fixed reflective film 54 and the movable reflective film 55 are arranged to be opposed to each other across an inter-reflective film gap G1. In the variable wavelength interference filter 5, an electrostatic actuator 56, which is the actuator according to the embodiment of the invention, is provided. The electrostatic actuator 56 is used to adjust a distance (a dimension) of the inter-reflective film gap G1. The electrostatic actuator 56 includes a fixed electrode 561 provided on the fixed substrate 51 and a movable electrode 562 provided on the movable substrate 52. The fixed electrode 561 and the movable electrode 562 are opposed to each other across an inter-electrode gap G2 (G2>G1). The electrodes 561 and 562 may be configured to be directly provided on the substrate surfaces of the fixed substrate 51 and the movable substrate 52 or may be configured to be provided via other film members.

In this embodiment, a configuration in which the inter-reflective film gap G1 is formed smaller than the inter-electrode gap G2 is illustrated. However, for example, depending on a wavelength region transmitted by the variable wavelength interference filter 5, the inter-reflective film gap G1 may be formed larger than the inter-electrode gap G2.

In the filter plan view, one side (e.g., a side between a vertex C1 and a vertex C2 in FIG. 3) of the fixed substrate 51 projects further to the outer side than the movable substrate 52. A projecting section of the fixed substrate 51 is a non-joining section 516 not joined to the movable substrate 52. In the non-joining section 516 of the fixed substrate 51, a surface exposed when the variable wavelength interference filter 5 is viewed from the movable substrate 52 side forms a first electric surface 514.

In the filter plan view, among the sides of the movable substrate 52, one side (a side between a vertex C3 and a vertex C4) opposed to the first electric surface 514 projects further to the outer side than the fixed substrate 51. A projecting section of the movable substrate 52 is a non-joining section 526 not joined to the fixed substrate 51. In the non-joining section 526 of the movable substrate 52, a surface exposed when the variable wavelength interference filter 5 is viewed from the fixed substrate 51 side forms a second electric surface 524.

2-1. Configuration of the Fixed Substrate

The fixed substrate 51 is formed by machining a glass base material formed to a thickness of, for example, about 500 μm. Specifically, as shown in FIG. 4, in the fixed substrate 51, an electrode arrangement groove 511 and a reflective-film setting section 512 are formed by etching. The fixed substrate 51 is formed to a thickness dimension larger than that of the movable substrate 52. The fixed substrate 51 does not bend because of electrostatic attraction caused when voltage is applied between the fixed electrode 561 and the movable electrode 562 and internal stress of the fixed electrode 561.

The electrode arrangement groove 511 is formed in an annular shape centering on a plane center point O of the variable wavelength interference filter 5 in the filter plan view. The reflective-film setting section 512 is formed to project to the movable substrate 52 side from the center portion of the electrode arrangement groove 511 in the plan view as shown in FIG. 4. The groove bottom surface of the electrode arrangement groove 511 is an electrode setting surface 511A on which the fixed electrode 561 is arranged. The projecting distal end face of the reflective-film setting section 512 is a reflective-film setting surface 512A.

In the fixed substrate 51, an electrode extraction groove 511B extending from the electrode arrangement groove 511 toward the first electric surface 514 and the second electric surface 524 is provided.

The fixed electrode 561 is provided on the electrode setting surface 511A of the electrode arrangement groove 511. The fixed electrode 561 is provided in a region of the electrode setting surface 511A opposed to the movable electrode 562 of a movable section 521 explained below. An insulating film for securing insulation properties between the fixed electrode 561 and the movable electrode 562 may be laminated on the fixed electrode 561.

On the fixed substrate 51, a fixed extracting electrode 563 extending from the outer circumferential edge of the fixed electrode 561 to the first electric surface 514 through the electrode extraction groove 511B is provided. The extension distal end portion (a portion located at the vertex C1 of the fixed substrate 51) of the fixed extracting electrode 563 forms a fixed electrode pad 563P on the first electric surface 514. The fixed electrode pad 563P is a first terminal extracting section.

In this embodiment, one fixed electrode 561 is provided on the electrode setting surface 511A. However, for example, two electrodes concentric around the plane center point O may be provided (a double electrode configuration).

As explained above, the reflective-film setting section 512 includes, coaxially with the electrode arrangement groove 511, the reflective-film setting surface 512A formed in a substantially columnar shape having a diameter dimension smaller than the electrode arrangement groove 511 and opposed to the movable substrate 52 of the reflective-film setting section 512.

As shown in FIG. 4, the fixed reflective film 54 is set in the reflective-film setting section 512. As the fixed reflective film 54, for example, a metal film of Ag or the like or an alloy film of an Ag alloy or the like can be used. For example, a dielectric multilayer film in which a high refractive layer is made of $TiO_2$ and a low refractive layer is made of $SiO_2$ may be used. Further, for example, a reflective film formed by laminating a metal film (or an alloy film) on the dielectric multilayer film, a reflective film formed by laminating the dielectric multilayer film on a metal film (or an alloy film), or a reflective film formed by laminating a single refractive layer ($TiO_2$ or $SiO_2$) and a metal film (or an alloy film) may be used.

A surface of the fixed substrate 51 on which the fixed reflective film 54 is not provided is a light incident surface 51A as shown in FIG. 4. A reflection preventing film may be formed in a position corresponding to the fixed reflective film on the light incident surface 51A. The reflection preventing film can be formed by alternately laminating a low refractive index film and a high refractive index film. The reflection preventing film reduces the reflectance of visible light on the surface of the fixed substrate 51 and increases the transmittance of the visible light.

Further, on the light incident surface 51A of the fixed substrate 51, as shown in FIG. 4, a non-translucent member 515 formed of Cr or the like is provided (in FIG. 3, the non-translucent member 515 is not shown). The non-translucent member 515 is formed in an annular shape, preferably, in a ring shape. The annular inner diameter of the non-translucent member 515 is set to an effective diameter for causing the fixed reflective film 54 and the movable reflective film 55 to interfere with light. Consequently, the non-translucent member 515 functions as an aperture for limiting incident light made incident on the optical filter device 600.

Among surfaces of the fixed substrate 51 opposed to the movable substrate 52, a surface on which the electrode arrangement groove 511, the reflective-film setting section 512, and the electrode extraction groove 511B are not formed by etching forms the first joining section 513. The first joining film 531 is provided on the first joining section 513. The first joining film 531 is joined to the second joining film 532 provided on the movable substrate 52, whereby the fixed substrate 51 and the movable substrate 52 are joined as explained above.

2-2. Configuration of the Movable Substrate

The movable substrate 52 is formed by machining a glass base material formed to a thickness of, for example, 200 μm.

Specifically, the movable substrate 52 includes, in the filter plan view shown in FIG. 3, the movable section 521 having a circular shape centering on the plane center point O, a holding section 522 provided on the outer side of the movable section 521 and configured to hold the movable section 521, and a substrate outer peripheral section 525 provided on the outer side of the holding section 522.

The movable section 521 is formed to a thickness dimension larger than that of the holding section 522. For example, in this embodiment, the movable section 521 is formed to the same dimension as the thickness dimension of the movable substrate 52. The movable section 521 is formed to a diameter dimension at least larger than the diameter dimension of the outer circumferential edge of the reflective-film setting surface 512A in the filter plan view. In the movable section 521, the movable electrode 562 and the movable reflective film 55 are provided.

Like the fixed substrate 51, a reflection preventing film may be formed on a surface of the movable section 521 on the opposite side of the fixed substrate 51. The reflection preventing film can be formed by alternately laminating a low refractive index film and a high refractive index film. It is possible to reduce the reflectance of visible light on the surface of the movable substrate 52 and increase the transmittance of the visible light. In this embodiment, a surface of the movable section 521 opposed to the fixed substrate 51 is a movable surface 521A.

The movable electrode 562 is opposed to the fixed electrode 561 across the inter-electrode gap G2 and is formed in an annular shape same as the shape of the fixed electrode 561. The movable substrate 52 includes a movable extracting electrode 564 extending from the outer circumferential edge of the movable electrode 562 toward the second electric surface 524. The extension distal end portion (a portion located at the vertex C3 of the movable substrate 52) of the movable extracting electrode 564 forms a movable electrode pad 564P on the second electric surface 524. The movable electrode pad 564P is the second terminal extracting section according to the embodiment of the invention.

The movable reflective film 55 is provided to be opposed to the fixed reflective film 54 across the inter-reflective film gap G1 in the center portion of the movable surface 521A of the movable section 521. As the movable reflective film 55, a reflective film having a configuration that is the same as the configuration of the fixed reflective film 54 is used.

The holding section 522 is a diaphragm that surrounds the circumference of the movable section 521. The holding section 522 is formed to a thickness dimension smaller than the thickness dimension of the movable section 521.

The holding section 522 more easily bends than the movable section 521. The movable section 521 can be easily displaced to the fixed substrate 51 side by slight electrostatic attraction. The thickness dimension of the movable section 521 is larger than the thickness dimension of the holding section 522. The movable section 521 has larger rigidity. Therefore, even when the holding section 522 is pulled to the fixed substrate 51 side by electrostatic attraction, no shape change of the movable section 521 occurs. Therefore, the movable reflective film 55 provided in the movable section 521 does not bend. It is possible to always maintain the fixed reflective film 54 and the movable reflective film 55 in a parallel state.

In this embodiment, the holding section 522 having a diaphragm shape is illustrated. However, the holding section 522 is not limited to this. For example, a configuration in which holding sections having a beam shape arranged at an equal angular interval around the plane center point O may be adopted.

As explained above, the substrate outer peripheral section 525 is provided on the outer side of the holding section 522 in the filter plan view. A surface of the substrate outer peripheral section 525 opposed to the fixed substrate 51 includes the second joining section 523 opposed to the first joining section 513. The second joining film 532 is provided in the second joining section 523. As explained above, the second joining film 532 is joined to the first joining film 531, whereby the fixed substrate 51 and the movable substrate 52 are joined.

3. Configuration of the Housing

Referring back to FIGS. 1 and 2, the housing 601 includes a base substrate 610, a lid 620, a base side glass substrate 630 (a light transmitting substrate), and a lid side glass substrate 640 (a light transmitting substrate).

The base substrate 610 is formed by, for example, a single-layer ceramic substrate. On the base substrate 610, the movable substrate 52 of the variable wavelength interference filter 5 is set.

In this embodiment, a fixing member 7 is arranged between the movable substrate 52 and the base substrate 610. In a plan view in which the movable substrate 52 is viewed from the substrate thickness dimension, the movable substrate 52 is fixed to the base substrate 610 by the fixing member 7 in one place excluding a region where the movable reflective film 55 is provided.

As shown in FIG. 2, the fixing member 7 is arranged in a position further on the inner side (closer to the plane center point O) than the projecting section (the non-joining section 526) of the movable substrate 52 and corresponding to the first joining section 513 and the second joining section 523. Further, the position of the fixed member 7 relative to the movable substrate 52 is indicated by an alternate long and two short dashes line in the filter plan view shown in FIG. 3. As shown in FIG. 3, the fixing member 7 is arranged in a position overlapping the first joining section 513 and the second joining section 523 and on the side connecting the vertex C1 and the vertex C4 (the outer peripheral portion of the movable substrate 52). In this way, the fixing member 7 is arranged in the predetermined place rather than being arranged over the entire surface between the base substrate 610 and the movable substrate 52.

A fixing place of the fixing member 7 is one place. It is desirable to appropriately set the shape (a setting area, height, etc.) of the fixing place taking into account the fixing intensity to the movable substrate 52 and the base substrate 610 and a degree of stress transmission due to a difference between the coefficients of thermal expansion of the members.

The fixing member 7 may be any member as long as the member can fix the movable substrate 52 and the base substrate 610. Examples of the member include epoxy and silicon adhesives. When an adhesive is used as the fixing member 7, it is desirable to use an adhesive that only contracts a little during hardening. In this case, it is desirable to apply the adhesive to only one point of the base substrate 610 by an application device such as a dispenser and fix the movable substrate 52 at the one point.

Alternatively, the fixing member 7 may be, for example, a member that physically engage or fit the movable substrate 52 and the base substrate 610.

In the base substrate 610, a light passing hole 611 is opened and formed in a region opposed to the reflective films (the fixed reflective film 54 and the movable reflective film 55) of the variable wavelength interference filter 5.

On a base inner side surface 612 (a lid opposed surface) opposed to the lid 620 of the base substrate 610, inner side terminal sections 615 connected to the electrode pads 563P and 564P on the first electric surface 514 and the second electric surface 524 of the variable wavelength interference filter 5 are provided. For the connection of the electrode pads 563P and 564P and the inner side terminal sections 615, for example, an FPC (Flexible Printed Circuits) 615A can be used. The electrode pads 563P and 564P and the inner side terminal sections 615 are joined by an Ag paste, an ACF (Anisotropic Conductive Film), an ACP (Anisotropic Conductive Paste), or the like. It is desirable to use the Ag paste with little degassing (emission of gas) in order to maintain an inner space 650 in a vacuum state. The connection is not limited to the connection by the FPC 615A. Wire connection by wire bonding or the like may also be carried out.

In the base substrate 610, through-holes 614 are formed to correspond to positions where the inner side terminal sections 615 are provided. The inner side terminal sections 615 are connected to, via the through-holes 614, outer side terminal sections 616 provided on a base outer side surface 613 on the opposite side of the base inner side surface 612 of the base substrate 610. In the through-holes 614, a metal member (e.g., Ag paste) for connecting the inner side terminal sections 615 and the outer side terminal sections 616 is filled in the through-holes 614. As such, air tightness of the inner space 650 of the housing 601 is maintained.

A base joining section 617 joined to the lid 620 is provided in the outer peripheral portion of the base substrate 610.

As shown in FIGS. 1 and 2, the lid 620 includes a lid joining section 624 joined to the base joining section 617 of the base substrate 610, a sidewall section 625 configured to extend from the lid joining section 624 and rise in a direction away from the base substrate 610, and a top surface section 626 configured to extend from the sidewall section 625 and cover the fixed substrate 51 side of the variable wavelength interference filter 5. The lid 620 can be formed of an alloy such as Kovar or metal.

The lid joining section 624 and the base joining section 617 of the base substrate 610 are joined, whereby the lid 620 is closely attached to and joined to the base substrate 610.

Examples of a method of the joining include, besides laser welding, soldering using silver wax or the like, sealing using a eutectic alloy, welding using low-melting point glass, glass depositing, glass flit joining, and bonding by epoxy resin. These methods for the joining can be selected as appropriate according to materials of the base substrate 610 and the lid 620, a joining environment, and the like.

In this embodiment, a pattern for joining 617A formed of Ni, Au, or the like is formed on the base joining section 617 of the base substrate 610. A high-power laser (e.g., a YAG laser) is irradiated on the formed pattern for joining 617A and the lid joining section 624 to perform laser joining.

The top surface section 626 of the lid 620 is parallel to the base substrate 610. In the top surface section 626, a light passing hole 621 is opened and formed in a region opposed to the reflective films 54 and 55 of the variable wavelength interference filter 5.

In this embodiment, light is made incident from the light passing hole 621 of the lid 620. The light extracted by the variable wavelength interference filter 5 is emitted from the light passing hole 611 of the base substrate 610. In such a configuration, in the light made incident from the light passing hole 621, only light having the effective diameter of the non-translucent member 515 provided on the light incident surface 51A of the variable wavelength interference filter 5 is made incident on the fixed reflective film 54 and the movable reflective film 55. In particular, the substrates 51 and 52 of the variable wavelength interference filter 5 are subjected to shape formation by etching. Curved surface sections are formed in etched portions due to the influence of side etching. When light is made incident on the curved surface sections, the light sometimes changes to stray light and is emitted from the light passing hole 611. On the other hand, in this embodiment, it is possible to prevent the occurrence of such stray light with the non-translucent member 515 and extract light having the desired target wavelength.

The base side glass substrate 630 is a glass substrate joined to a base outer side surface 631 of the base substrate 610 to cover the light passing hole 611. The base side glass substrate 630 is formed to a size larger than the light passing hole 611. The plane center point O of the base side glass substrate 630 is arranged to coincide with the plane center point O of the light passing hole 611. The plane center point O coincides with the plane center point O of the variable wavelength interference filter 5 and coincides with the plane center point O of the fixed reflective film 54, the movable reflective film 55, and the annular inner circumferential edge of the non-translucent member 515. In the base side glass substrate 630, in a plan view in which the optical filter device 600 is viewed from the thickness direction of the base substrate 610 (the base side glass substrate 630), a region further on the outer side than an outer circumferential edge 611A of the light passing hole 611 (a region from the outer circumferential edge 611A to the substrate end edge 631 of the base side glass substrate 630) is joined to the base substrate 610.

The lid side glass substrate 640 is a glass substrate joined to a lid inner side surface 622 side on the opposite side of the light passing hole 621 opposed to the base substrate 610 of the lid 620 to cover the light passing hole 621. The lid side glass substrate 640 is formed in a size larger than the light passing hole 621. The plane center point O of the lid side glass substrate 640 is arranged to coincide with the plane center point O of the light passing hole 621. In the lid side glass substrate 640, in a plan view in which the optical filter device 600 is viewed from the thickness direction of the base substrate 610 (the lid side glass substrate 640), a region further on an outer circumferential edge 621A of the light passing hole 621 (a region from the outer circumferential edge 621A to a substrate end edge 641 of the lid side glass substrate 640) is joined to the lid 620.

As the joining of the base substrate 610 and the base side glass substrate 630 and the joining of the lid 620 and the lid side glass substrate 640, glass flit joining using glass flits, which are chips of glass obtained by melting a glass material at high temperature and rapidly cooling the glass material, can be used. In the glass flit joining, a gap does not occur in a joined portion. It is possible to maintain the inner space 650 in a vacuum state by using glass flits with little degassing (emission of gas). The joining is not limited to the glass flit joining. Joining by welding using low-melting point glass, glass sealing, or the like may be performed. For example, only for the purpose of suppressing intrusion of foreign matters into the inner space 650, bonding by epoxy resin or the like may be performed, although it is not suitable for maintaining the vacuum state of the inner space 650.

As explained above, in the optical filter device 600 according to this embodiment, the inner space 650 of the housing 601 is maintained air tight by the joining of the base substrate 610 and the lid 620, the joining of the base substrate 610 and the base side glass substrate 630, and the joining of the lid 620 and the lid side glass substrate 640. In this embodiment, the inner space 650 is maintained in the vacuum state.

Since the inner space 650 is maintained in the vacuum state, when the movable section 521 of the variable wavelength interference filter 5 is moved, air resistance does not occur. Therefore, responsiveness can be improved.

Manufacturing Method for the Optical Filter Device

A manufacturing method for the optical filter device 600 explained above is explained on the basis of the drawings.

Figure 5:
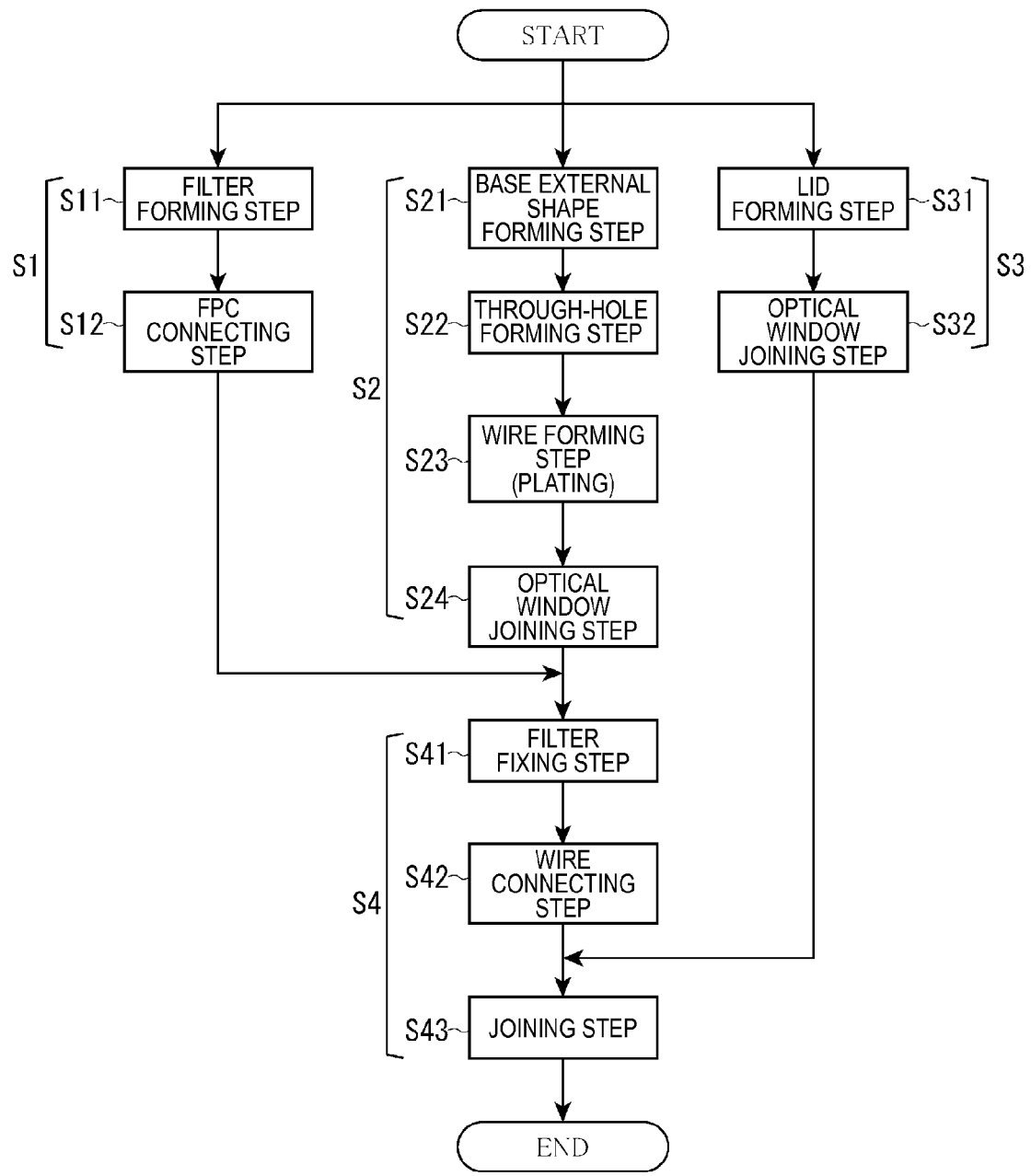
FIG. 5 is a process chart for explaining a manufacturing process for the optical filter device according to the first embodiment.

FIG. 5 is a process chart for explaining a manufacturing process for manufacturing the optical filter device 600.

In the manufacturing of the optical filter device 600, first, a filter preparing step (S1) for manufacturing the variable wavelength interference filter 5 included in the optical filter device 600, a base-substrate preparing step (S2), and a lid preparing step (S3) is carried out.

Filter Preparing Step

In the filter preparing step in S1, first, a filter forming step for manufacturing the variable wavelength interference filter 5 is carried out (S11).

In S11, the fixed substrate 51 and the movable substrate 52 are formed by etching or the like as appropriate. On the fixed substrate 51, after the fixed electrode 561 and the fixed extracting electrode 563 are formed, the non-translucent member 515 is formed and, thereafter, the fixed reflective film 54 is formed. On the movable substrate 52, after the movable electrode 562 is formed, the movable reflective film 55 is formed.

Thereafter, the fixed substrate 51 and the movable substrate 52 are joined via the joining film 53, whereby the variable wavelength interference filter 5 is obtained. In this embodiment, in the filter forming step (S11), the fixed substrate 51 and the movable substrate 52 are joined to form the non-joining section 516 and the non-joining section 526.

Thereafter, an FPC connecting step for connecting the FPC 615A to the fixed electrode pad 563P and the movable electrode pad 564P of the variable wavelength interference filter 5 obtained in S11 is carried out (S12). In the connection of the FPC 615A and the electrode pads 563P and 564P, an Ag paste with little degassing is used.

Base-Substrate Preparing Step

In the base-substrate preparing step in S2, first, a base-external-shape forming step is carried out (S21). In S21, a substrate before baking formed by laminating a sheet, which is a material forming a ceramic substrate, is cut as appropriate to form the shape of the base substrate 610 including the light passing hole 611. The substrate before baking is baked to form the base substrate 610.

The light passing hole 611 may be formed in the baked and formed base substrate 610 by machining using a high-power laser such as a YAG laser.

Subsequently, a through-hole forming step for forming the through-holes 614 in the base substrate 610 is carried out (S22). In S22, in order to form the fine through-holes 614, laser machining using the YAG laser or the like is carried out. In the formed through-holes 614, a conductive member having high adhesion to the base substrate 610 is filled.

Thereafter, a wire forming step for forming the inner side terminal sections 615 and the outer side terminal sections 616 on the base substrate 610 is carried out (S23).

In S23, for example, plating using metal such as Ni/Au is carried out to form the inner side terminal sections 615 and the outer side terminal sections 616. When the base joining section 617 and the lid joining section 624 are joined by laser welding, plating of Ni or the like is applied to the base joining section 617 to form the pattern for joining 617A.

Thereafter, an optical-window joining step for joining the base side glass substrate 630 for covering the light passing hole 611 to the base substrate 610 is carried out (S24).

In S24, alignment adjustment is carried out such that the plane center of the base side glass substrate 630 and the plane center of the light passing hole 611 coincide with each other. The base side glass substrate 630 is joined to the base substrate 610 by flit glass joining using flit glass.

Lid Preparing Step

In the lid preparing step in S3, first, a lid forming step for forming the lid 620 is carried out (S31). In S31, a metal substrate formed of Kovar or the like is pressed to form the lid 620 including the light passing hole 621.

Thereafter, an optical-window joining step for joining the lid side glass substrate 640 for covering the light passing hole 621 to the lid 620 is carried out (S32).

In S32, alignment adjustment is carried out such that the plane center of the lid side glass substrate 640 and the plane center of the light passing hole 621 coincide with each other. The lid side glass substrate 640 is joined to the lid 620 by flit glass joining using flit glass.

Device Assembling Step

A device assembling step for joining the variable wavelength interference filter 5, the base substrate 610, and the lid 620 obtained in S1 to S3 to form the optical filter device 600 is carried out (S4).

In S4, first, a filter fixing step for fixing, with the fixing member 7, the variable wavelength interference filter 5 to the base substrate 610 is carried out (S41). In this embodiment, as explained above, the substrate outer peripheral section 525 of the movable substrate 52 is fixed to the base substrate 610 using the fixing member 7 in the position shown in FIGS. 2 and 3. As the fixing member 7, in this embodiment, an adhesive is used. First, in S41, the adhesive is applied to one point in a predetermined position of the base substrate 610. Alignment adjustment is carried out such that the plane center points O of the fixed reflective film 54 and the movable reflective film 55 coincide with the plane center point O of the light passing hole 611. After the alignment adjustment, the movable substrate 52 is stuck to the base substrate 610 and the adhesive is hardened. The variable wavelength interference filter 5 is fixed to the base substrate 610 in this way.

Thereafter, a wire connecting step is carried out (S42). In S42, the other end portion of the FPC 615A connected to the variable wavelength interference filter 5 in S12 is stuck to the inner side terminal sections 615 of the base substrate 610. Consequently, the inner side terminal sections 615 and the fixed electrode pad 563P and the movable electrode pad 564P are connected. In this connection, as in the connection explained above, it is desirable to use the Ag paste with little degassing.

Thereafter, a joining step for joining the base substrate 610 and the lid 620 is carried out (S43). In S43, for example, in a vacuum chamber device, the base substrate 610 and the lid 620 are placed one on top of the other under an environment set to a vacuum atmosphere. The base substrate 610 and the lid 620 are joined by laser joining using the YAG laser or the like. In the laser joining, since only a joining section is locally heated and joined, it is possible to suppress a temperature rise in the inner space 650. Therefore, it is possible to prevent an inconvenience that the reflective films 54 and 55 of the variable wavelength interference filter 5 are deteriorated by high temperature.

Consequently, the optical filter device 600 is manufactured.

Action and Effects of the Embodiment

In this embodiment, the optical filter device 600 includes the variable wavelength interference filter 5 and the housing 601 configured to house the variable wavelength interference filter 5. The housing 601 includes the base substrate 610 and the lid 620 joined to the base substrate 610. The movable substrate 52 of the variable wavelength interference filter 5 and the base substrate 610 are fixed in one place by the fixing member 7.

In the optical filter device in which the fixing member 7 is arranged over the entire surface between the movable substrate 52 and the base substrate 610 or arranged at two or more points, stress due to a difference between the coefficients of thermal expansion of the movable substrate 52 and the fixing member 7 and a difference between the coefficients of thermal expansion of the base substrate 610 and the fixing member 7 tends to act over the entire movable substrate 52. When the adhesive is used as the fixing member 7, stress due to contraction caused when the adhesive is hardened tends to act over the entire movable substrate 52. Since the movable substrate 52 is joined to the fixed substrate 51, stress tends to act on the fixed substrate 51. When the stress acts, the fixed reflective film 54 of the fixed substrate 51 and the movable reflective film 55 of the movable substrate warp and the optical characteristics of the variable wavelength interference filter 5 are affected.

On the other hand, in the optical filter device 600, as explained above, the movable substrate 52 and the base substrate 610 are fixed in one place by the fixing member 7. Therefore, stress due to a difference between coefficients of thermal expansion and contract stress during adhesive hardening less easily act on the movable substrate 52 and the fixed substrate 51. As a result, with the optical filter device 600, it is possible to suppress warping of the fixed reflective film 54 of the fixed substrate 51 and the movable reflective film 55 of the movable substrate 52.

Second Embodiment

A second embodiment of the invention is explained on the basis of the drawings.

In the optical filter device 600 according to the first embodiment explained above, the movable substrate 52 is fixed to the base substrate 610 in one place by the fixing member 7.

Figure 6:
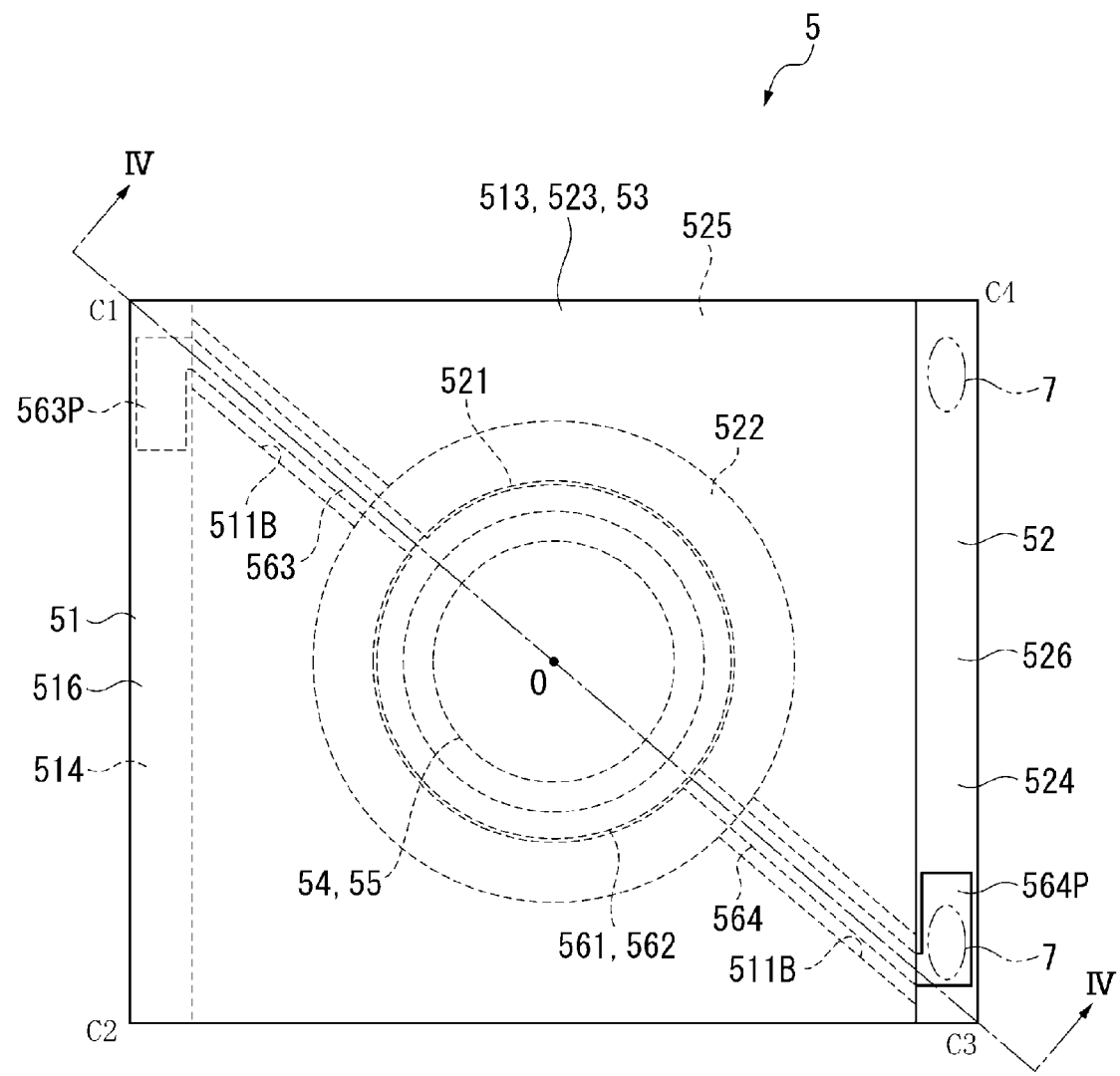
FIG. 6 is a plan view showing a schematic configuration of an interference filter housed in an optical filter device according to a second embodiment and is a diagram for explaining a positional relation between the interference filter and a fixing member.

On the other hand, in an optical filter device 600A (see FIG. 7) according to the second embodiment, the variable wavelength interference filter 5 is fixed to the base substrate 610 in two places by the fixing member 7 (see FIG. 6). The configuration of the optical filter device 600A is explained in detail below.

FIG. 6 is a plan view showing a schematic configuration of the variable wavelength interference filter 5 housed in the optical filter device 600A according to the second embodiment and is a diagram for explaining a positional relation between the variable wavelength interference filter 5 and the fixing member 7.

Figure 7:
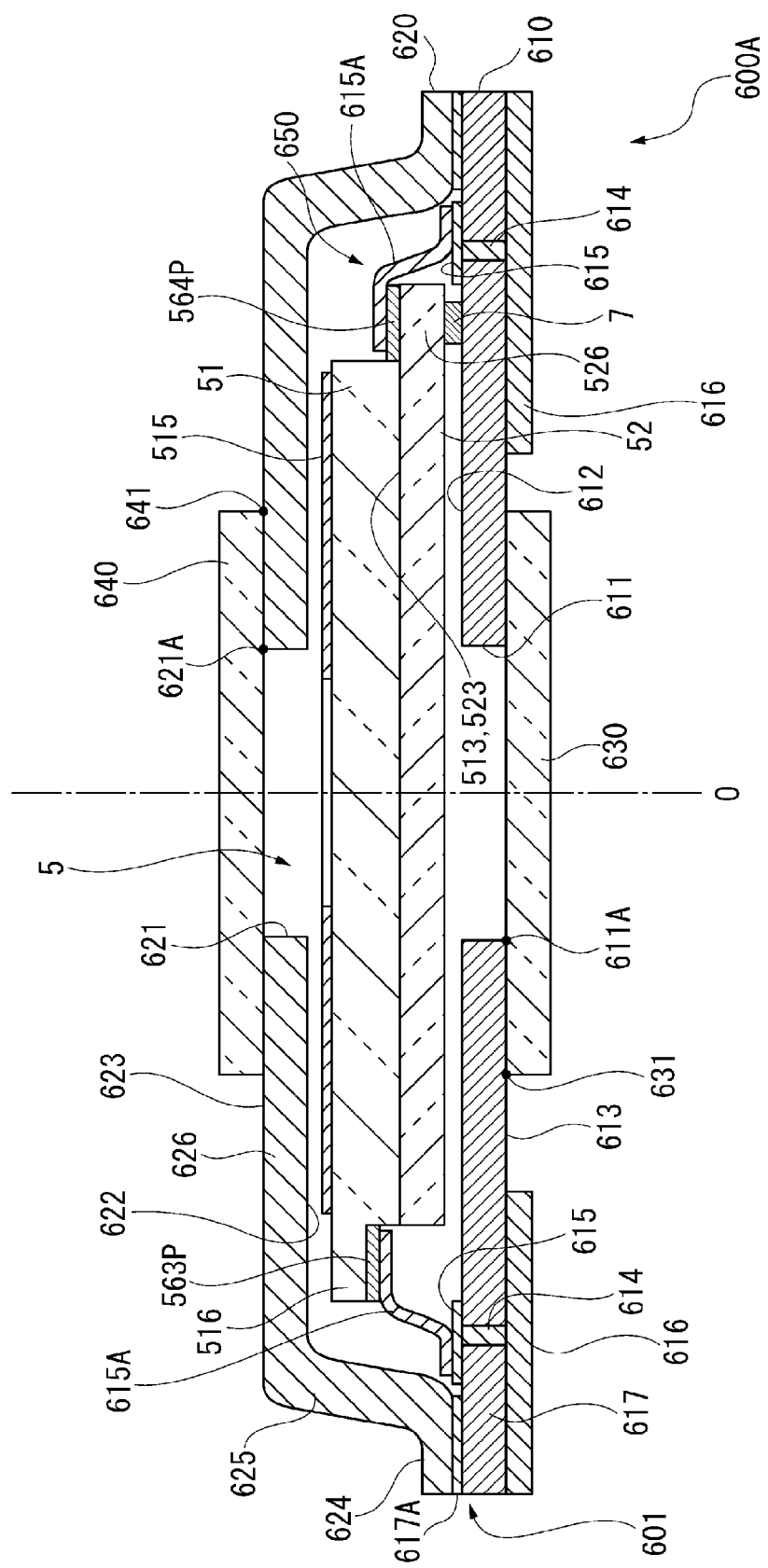
FIG. 7 is a sectional view showing a schematic configuration of the optical filter device according to the second embodiment.

FIG. 7 is a sectional view showing a schematic configuration of the optical filter device 600A according to the second embodiment.

Components that are the same as the components in the first embodiment are denoted by the same reference numerals and signs and an explanation of the components is omitted or simplified.

In the optical filter device 600A, as shown in FIG. 7, the fixing member 7 is arranged between the non-joining section 526 and the base substrate 610. The fixing member 7 fixes the movable substrate 52 to the base substrate 610 at a corner portion of the movable substrate 52 in a plan view in which the movable substrate 52 is viewed from the substrate thickness direction.

As shown in FIG. 6, the fixing members 7 are arranged in two places in total in the vicinity of the vertex C3 and in the vicinity of the vertex C4 of the variable wavelength interference filter 5. In this way, in this embodiment, the fixing members 7 fix the non-joining section 526 of the movable substrate 52 and the base substrate 610 in the two places. When the movable substrate 52 is formed in a rectangular shape, the fixing members 7 in the two places are desirably arranged along a short side of the outer peripheral portion of the movable substrate 52. This is because a space between the fixing places can be reduced.

The optical filter device 600A according to this embodiment can be manufactured in the same manner as the manufacturing method according to the first embodiment except that the arrangement places of the fixing members 7 are different as explained above.

For example, in S41 in the first embodiment, the adhesive used as the fixing members 7 is applied to two places on the surface of the base substrate 610. Specifically, the application places of the adhesive are places where the adhesive is in contact with the non-joining section 526 when the movable substrate 52 is fixed to the base substrate 610 after alignment adjustment.

Action and Effects of the Embodiment

In the optical filter device 600A, the movable substrate 52 and the base substrate 610 are fixed by the fixing members 7 arranged in the two places. Therefore, compared with the optical filter device in which the fixing member 7 is arranged over the entire surface between the movable substrate 52 and the base substrate 610, as in the first embodiment, stress due to a difference between the coefficients of thermal expansion of the members and contraction stress during adhesive hardening less easily acts on the movable substrate 52 and the fixed substrate 51. As a result, with the optical filter device 600A, it is possible to suppress warping of the fixed reflective film 54 and the movable reflective film 55.

In the optical filter device 600A, the non-joining section 526 of the movable substrate 52 and the base substrate 610 are fixed in the two places by the fixing members 7. In this way, in the optical filter device 600A, although the fixing places increase compared with the first embodiment, the fixing places are in the non-joining section 526. In other words, the fixing places are positions spaced apart from the first joining section 513 and the second joining section 523. Therefore, as explained above, the stress due to the difference between the coefficients of thermal expansion and the contraction stress during the adhesive hardening less easily acts not only on the movable substrate 52 but also on, in particular, the fixed substrate 51. In the optical filter device 600A, the fixing places are spaced apart from the places where the fixed reflective film 54 and the movable reflective film 55 are provided.

Therefore, with the optical filter device 600A, it is possible to suppress warping of the fixed reflective film 54 and the movable reflective film 55.

In the optical filter device 600A, the movable substrate 52 and the base substrate 610 are fixed in the two places by the fixing members 7. Therefore, it is likely that a moment due to the fixing in the two places affects the movable substrate 52 and the fixed substrate 51. For example, when the arrangement places of the fixing members 7 are two places in the vicinities of the vertex C1 and the vertex C3, a distance between the two places increases, the influence of the moment is large and warping of the reflective films 54 and 55 tends to occur. The holding section 522 is formed between the two places. Therefore, the holding section 522 bends due to the influence of the moment. As a result, it is likely that the inter-reflective film gap G1 cannot be accurately controlled.

However, in the optical filter device 600A, the fixing members 7 are arranged in the vicinities of the vertex C3 and the vertex C4 of the fixing member of the variable wavelength interference filter 5. As shown in FIG. 6, the variable wavelength interference filter 5 is, for example, an optical member having a rectangular tabular shape. Therefore, the fixing members 7 are arranged on both end sides of one side connected by the vertex C3 and the vertex C4. Therefore, the influence of the moment can be reduced.

Third Embodiment

A third embodiment of the invention is explained on the basis of the drawings.

In the optical filter device 600A according to the second embodiment, the variable wavelength interference filter 5 is fixed to the base substrate 610 in the two places by the fixing members 7.

In an optical filter device 600B (see FIG. 8) according to the third embodiment, as in the second embodiment, the variable wavelength interference filter 5 is fixed to the base substrate 610 in two places by the fixing members 7. However, the optical filter device 600B is different from the optical filter device 600A in that, as shown in FIG. 8, a substrate recess 527 is formed on a surface of the movable substrate 52 opposed to the base substrate 610.

The configuration of the optical filter device 600B is explained in detail below.

Figure 8:
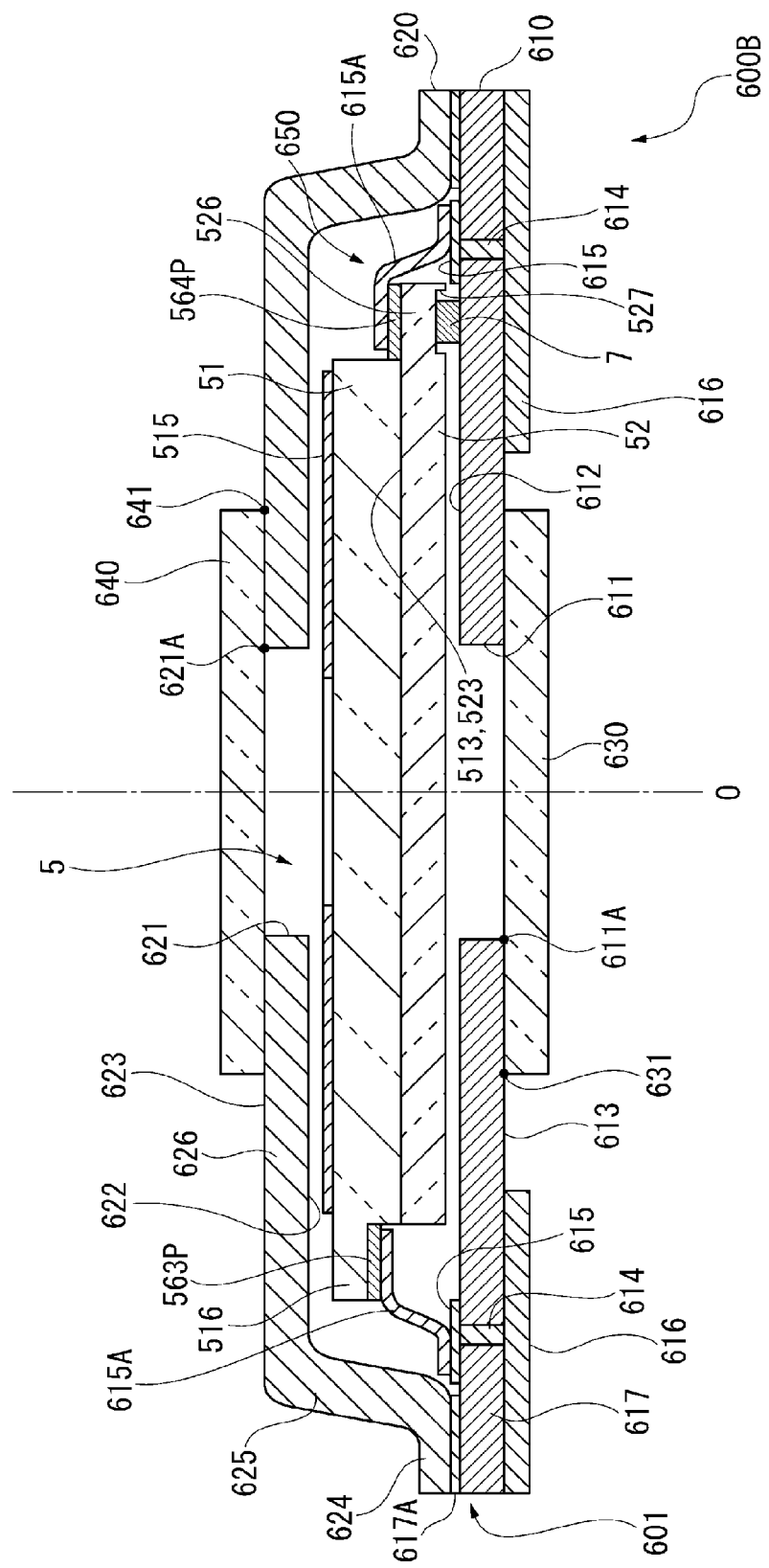
FIG. 8 is a sectional view showing a schematic configuration of an optical filter device according to a third embodiment.

FIG. 8 is a sectional view showing a schematic configuration of the optical filter device 600B according to the third embodiment.

Figure 9:
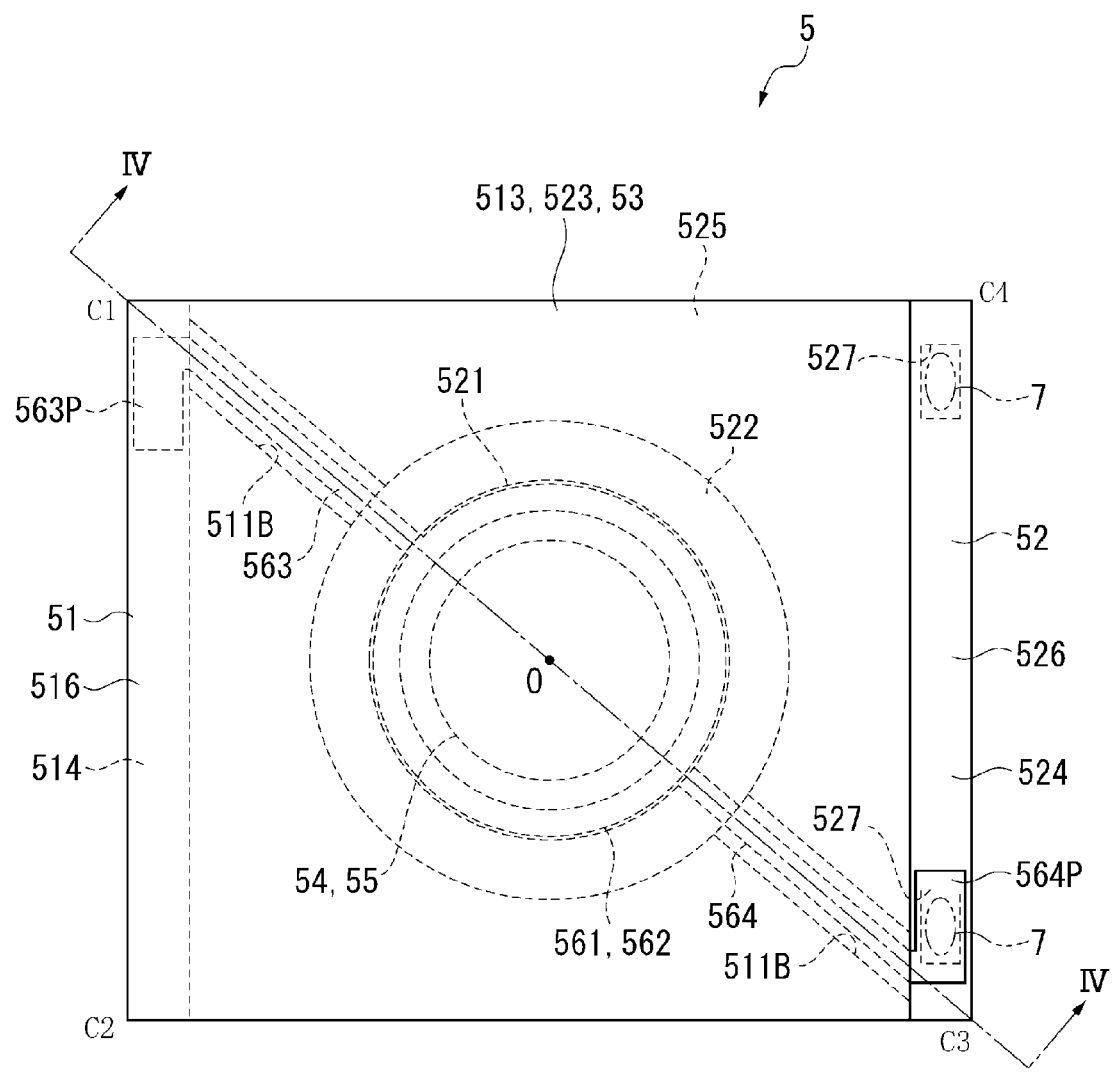
FIG. 9 is a plan view showing a schematic configuration of an interference filter housed in the optical filter device according to the third embodiment and is a diagram for explaining a positional relation between the interference filter and the fixing member.

FIG. 9 is a plan view showing a schematic configuration of the variable wavelength interference filter 5 housed in the optical filter device 600B according to the third embodiment and is a diagram for explaining a positional relation between the variable wavelength interference filter and the fixing members 7.

Components that are the same as the components in the first embodiment and the second embodiment are denoted by the same reference numerals and signs and an explanation of the components is omitted or simplified.

In this embodiment, as shown in FIG. 8, the substrate recess 527 is formed on a surface of the non-joining section 526 opposed to the base substrate 610. The substrate recess 527 is sunk in the thickness direction of the movable substrate 52 by a predetermined dimension. The substrate recess 527 can be formed by etching or the like in the same manner as the formation of the holding section 522.

The substrate recess 527 is formed in the non-joining section 526. Specifically, as shown in FIG. 9, the substrate recesses 527 are formed in two places in total in the vicinity of the vertex C3 and in the vicinity of the vertex C4 of the variable wavelength interference filter 5.

In this embodiment, the fixing members 7 are arranged to correspond to the two places where the substrate recesses 527 are formed. Therefore, the fixing members 7 fix the movable substrate 52 and the base substrate 610 in positions substantially the same as the positions in the second embodiment.

The optical filter device 600B according to this embodiment can be manufactured in the same manner as the manufacturing method according to the first embodiment except that the formation of the substrate recesses 527 is done and the arrangement places of the fixing members 7 are different as explained above.

For example, the substrate recesses 527 can be formed in the filter forming step in S11 in the first embodiment. In the etching of the movable substrate 52, the substrate recesses 527 may be simultaneously formed.

Action and Effect of the Embodiment

With the optical filter device 600B, the action and effects explained below are attained in addition to the action and effects that are the same as the action and effects of the optical filter device 600A according to the second embodiment.

In the optical filter device 600B, the substrate recesses 527 are formed on the movable substrate 52. Therefore, since the positions of the fixing members 7 are regulated by the substrate recesses 527, it is possible to more surely fix the movable substrate 52 and the base substrate 610 in desired places. For example, when a member having fluidity (e.g., an adhesive) is used as the fixing members 7, it is possible to suppress, with the substrate recesses 527, the fixing members 7 from oozing/sliding out of application positions.

Therefore, with the optical filter device 600B, since it is possible to surely arrange the fixing members 7 in desired places, it is possible to improve the quality and the yield of the optical filter device 600B.

Fourth Embodiment

A fourth embodiment of the invention is explained on the basis of the drawings.

In the optical filter device 600B according to the third embodiment, the substrate recesses 527 are formed on the surface of the movable substrate 52 opposed to the base substrate 610.

On the other hand, in an optical filter device 600C (see FIG. 10) according to this embodiment, although the substrate recesses 527 are not formed, base recesses 618 are formed on the base inner side surface 612 of the base substrate 610.

The configuration of the optical filter device 600B is explained in detail below.

Figure 10:
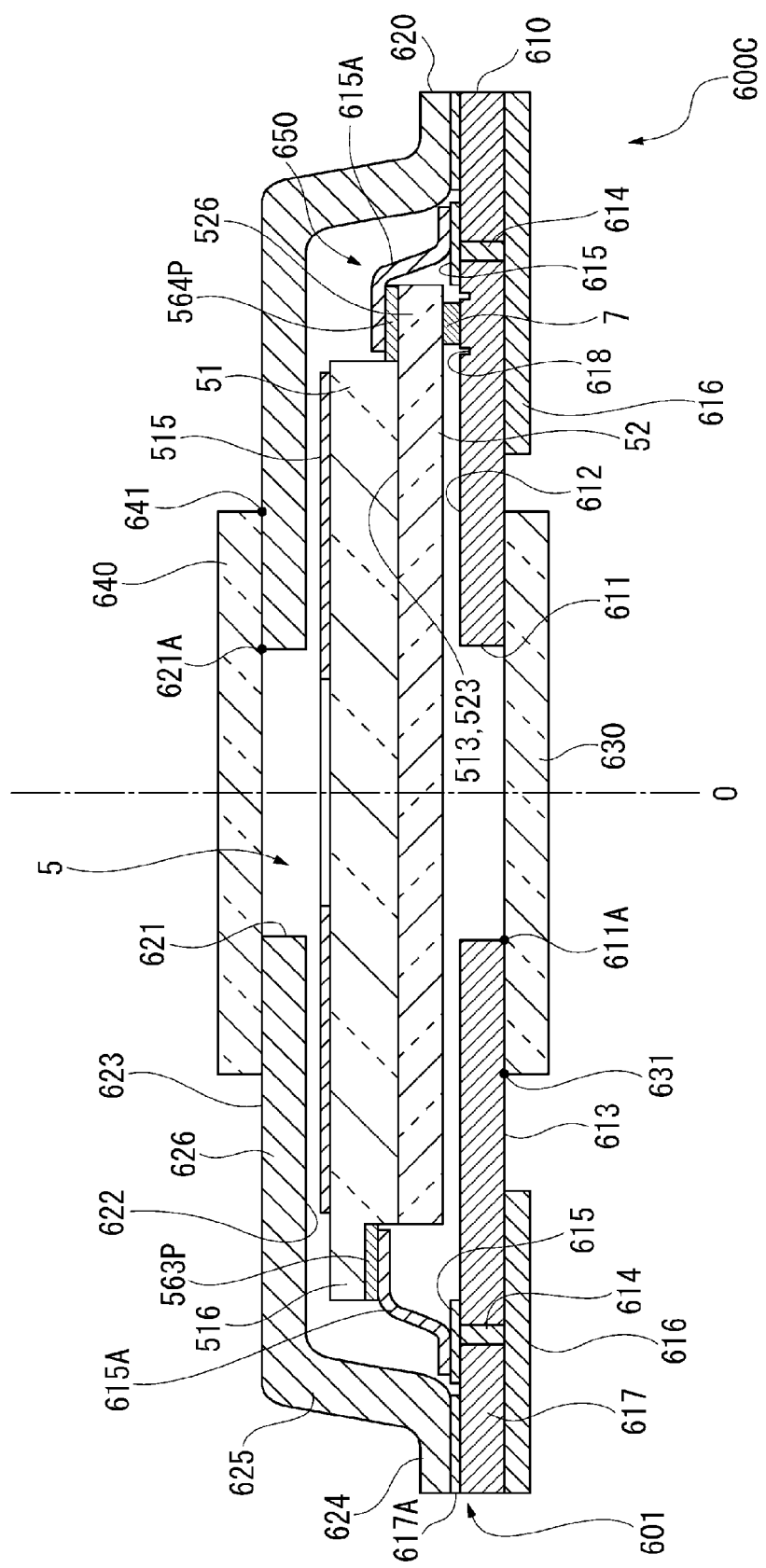
FIG. 10 is a sectional view showing a schematic configuration of an optical filter device according to a fourth embodiment.

FIG. 10 is a sectional view showing a schematic configuration of the optical filter device 600C according to the fourth embodiment.

Components that are the same as the components in the first to third embodiments are denoted by the same reference numerals and signs and an explanation of the components is omitted or simplified.

Arrangement positions of the fixing members 7 in the optical filter device 600C are the same as the arrangement places in the optical filter device 600A according to the second embodiment. Specifically, the fixing members 7 are arranged between the non-joining section 526 and the base substrate 610. The fixing members 7 are arranged in two places (positions corresponding to the vicinity of the vertex C3 and the vicinity of the vertex C4 of the variable wavelength interference filter 5).

In the optical filter device 600C, the base recesses 618 are formed to correspond to the arrangement places of the fixing members 7. The base recesses 618 are sunk in the base inner side surface 612 of the base substrate 610 by a predetermined dimension in the thickness direction of the base substrate 610. The base recesses 618 are formed for each of the arrangement places of the fixing members 7. In this embodiment, the base recesses 618 are formed to correspond to the respective arrangement places of the fixing members 7 in the two places. In this embodiment, the base recesses 618 are grooves formed to surround the fixing members 7.

The optical filter device 600C according to this embodiment can be manufactured in the same manner as the manufacturing method according to the first embodiment except that the formation of the base recesses 618 is done and the arrangement places of the fixing members 7 are different as explained above.

For example, the base recesses 618 can be formed in the base substrate preparing step in S2 in the first embodiment. When the light passing hole 611 is formed in the baked and formed base substrate 610 by machining using a high-power laser such as the YAG laser, the base recesses 618 may be simultaneously formed. When the through-holes 614 are formed, the base recesses 618 may be simultaneously formed.

Action and Effects of the Embodiment

With the optical filter device 600C, the action and effects explained below are attained in addition to the action and effects that are the same as the action and effects of the optical filter device 600A according to the second embodiment.

In the optical filter device 600C, the groove-like base recesses 618 are formed on the base substrate 610 to surround the fixing members 7. Therefore, when a member having fluidity (e.g., an adhesive) is used as the fixing members 7, it is possible to suppress, with the base recesses 618, the fixing members 7 from oozing/sliding out of application positions.

Therefore, with the optical filter device 600C, since it is possible to surely arrange the fixing members 7 in desired places, and it is possible to improve the quality and the yield of the optical filter device 600C.

Fifth Embodiment

A fifth embodiment of the invention is explained on the basis of the drawings.

In the optical filter device 600A according to the second embodiment, the non-joining section 526 of the movable substrate 52 and the base substrate 610 are fixed in the two places by the fixing members 7.

On the other hand, in an optical filter device according to this embodiment, the non-joining section 526 of the movable substrate 52 and the base substrate 610 are fixed in one place by the fixing member 7.

Figure 11:
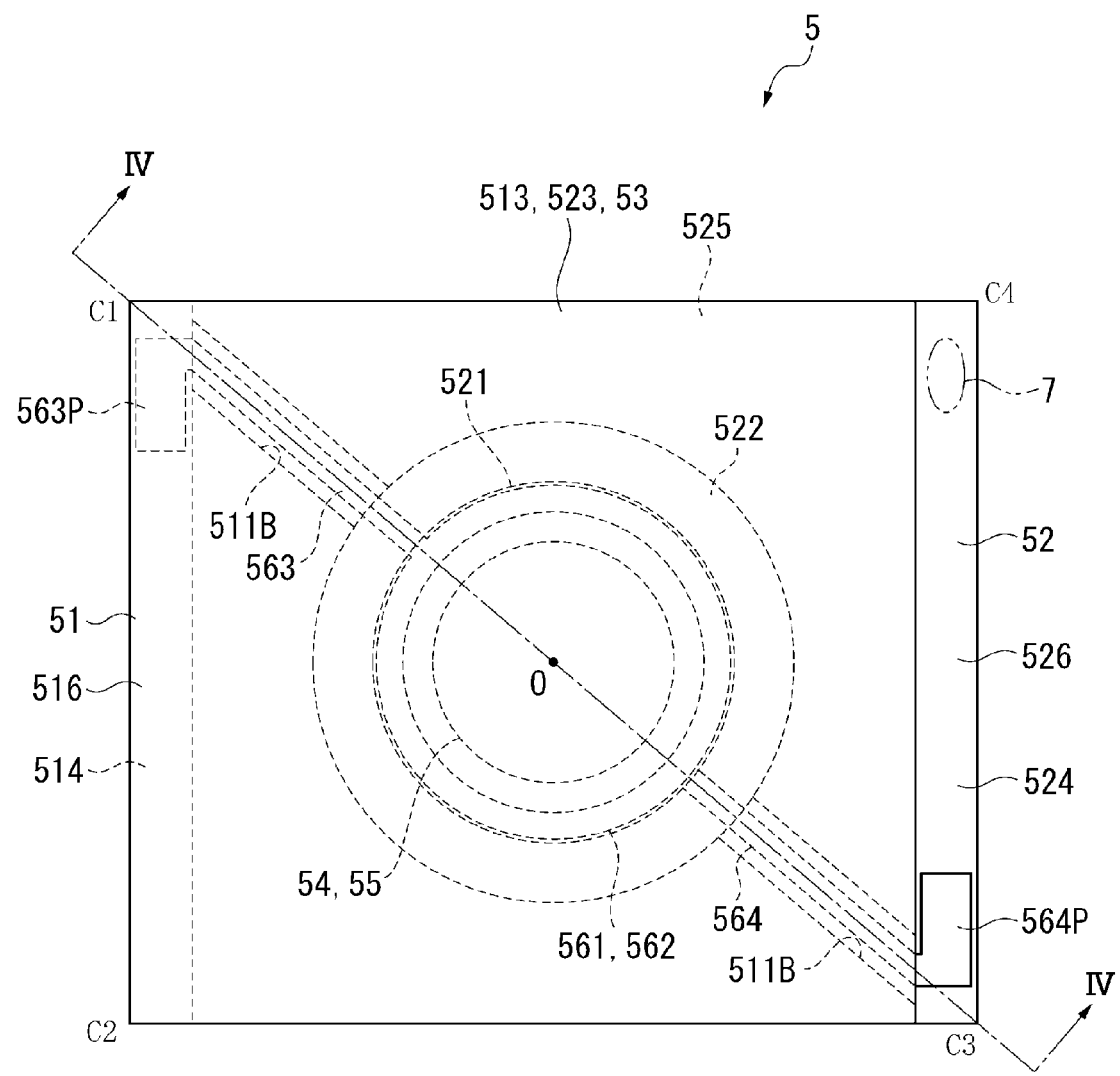
FIG. 11 is a plan view showing a schematic configuration of an interference filter housed in an optical filter device according to a fifth embodiment and is a diagram for explaining a positional relation between the interference filter and a fixing member.

FIG. 11 is a plan view showing a schematic configuration of the variable wavelength interference filter 5 housed in the optical filter device according to the fifth embodiment and is a diagram for explaining a positional relation between the variable wavelength interference filter 5 and the fixing member 7.

Components that are the same as the components in the first to fourth embodiments are denoted by the same reference numerals and signs and an explanation of the components is omitted or simplified.

In this embodiment, as shown in FIG. 11, the fixing member 7 is arranged in one place in the vicinity of the vertex C4 in the non-joining section 526 of the variable wavelength interference filter 5 and is not arranged in the portion of the movable electrode pad 564P, which is the second terminal extracting section. In this way, in this embodiment, the movable substrate 52 is fixed to a base substrate in one place at a corner portion.

Action and Effects of the Embodiment

With the optical filter device according to this embodiment, the action and effects explained below are attained.

In the optical filter device according to this embodiment, the non-joining section 526 of the movable substrate 52 and the base substrate 610 are fixed in one place by the fixing member 7. In this way, the fixing place is only one place spaced apart from the first joining section 513 and the second joining section 523. Therefore, the stress due to the difference between the coefficients of thermal expansion and the contraction stress during the adhesive hardening explained above much less easily act on the movable substrate 52 and the fixed substrate 51. Therefore, with the optical filter device according to this embodiment, it is possible to more surely suppress warping of the fixed reflective film 54 and the movable reflective film 55.

Sixth Embodiment

A sixth embodiment of the invention is explained on the basis of the drawings.

In the sixth embodiment, a colorimetric sensor 3, which is an optical module incorporating the optical filter device 600 according to the first embodiment, and a colorimetric apparatus 1, which is an electronic apparatus incorporating the optical filter device 600, are explained.

1. Schematic Configuration of the Colorimetric Apparatus

Figure 12:
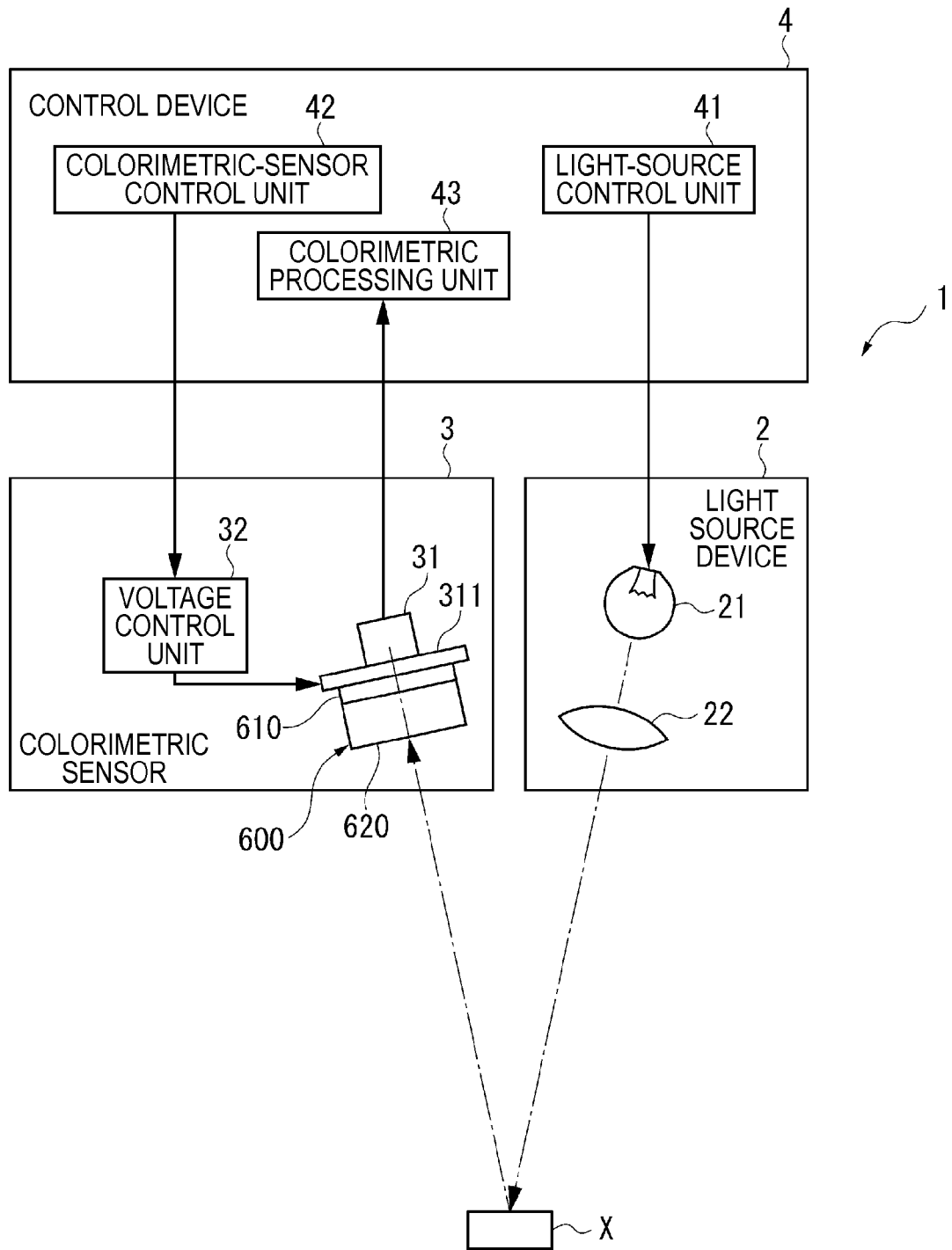
FIG. 12 is a block diagram showing a schematic configuration of a colorimetric apparatus in a sixth embodiment.

FIG. 12 is a block diagram showing a schematic configuration of the colorimetric apparatus 1 according to the sixth embodiment.

The colorimetric apparatus 1 is the electronic apparatus according to the embodiment of the invention. The colorimetric apparatus 1 includes, as shown in FIG. 12, a light source device 2 configured to emit light to a test target X, the colorimetric sensor 3, and a control device 4 configured to control the overall operation of the colorimetric apparatus 1. The colorimetric apparatus 1 is an apparatus that reflects the light emitted from the light source device 2 on the test target X, receives the reflected test target light in the colorimetric sensor 3, and analyzes and measures chromaticity of the test target light, i.e., a color of the test target X on the basis of a detection signal output from the colorimetric sensor 3.

2. Configuration of the Light Source Device

The light source device 2 includes a light source 21 and a plurality of lenses 22 (only one is shown in FIG. 12) and emits white light to the test target X. The plurality of lenses 22 may include a collimator lens. In this case, the light source device 2 changes the white light emitted from the light source 21 into parallel light using the collimator lens and emits the parallel light from a not-shown projection lens toward the test target X. In this embodiment, the colorimetric apparatus 1 including the light source device 2 is illustrated. However, for example, when the test target X is a light emitting member such as a liquid crystal panel, the light source device 2 does not have to be provided.

3. Configuration of the Colorimetric Sensor

The colorimetric sensor 3 configures the optical module according to the embodiment of the invention and includes the optical filter device 600 according to the first embodiment. The colorimetric sensor 3 includes, as shown in FIG. 12, the optical filter device 600, a detecting unit 31 configured to receive light transmitted through the variable wavelength interference filter 5 of the optical filter device 600, and a voltage control unit 32 configured to change the wavelength of the light transmitted through the variable wavelength interference filter 5.

The colorimetric sensor 3 includes, in a position opposed to the variable wavelength interference filter 5, a not-shown incident optical lens configured to guide the reflected light (the test target light) reflected by the test target X to the inside. The colorimetric sensor 3 splits, with the variable wavelength interference filter 5 in the optical filter device 600, light having predetermined wavelength in the test target light made incident from the incident optical lens and receives the split light in the detecting unit 31.

The detecting unit 31 includes a plurality of photoelectric conversion elements and generates an electric signal corresponding to a received light amount. The detecting unit 31 is connected to the control device 4 via, for example, a circuit board 311. The detecting unit 31 outputs the generated electric signal to the control device 4 as a light reception signal.

The outer side terminal sections 616 formed on the base outer side surface 613 of the base substrate 610 are connected to the circuit board 311. The circuit board 311 is connected to the voltage control unit 32 via a circuit formed in the circuit board 311.

With such a configuration, the optical filter device 600 and the detecting unit 31 can be integrally formed via the circuit board 311. The configuration of the colorimetric sensor 3 can be simplified.

The voltage control unit 32 is connected to the outer side terminal sections 616 of the optical filter device 600 via the circuit board 311. The voltage control unit 32 applies, on the basis of a control signal input from the control device 4, a predetermined step voltage between the fixed electrode pad 563P and the movable electrode pad 564P to drive the electrostatic actuator 56. Consequently, electrostatic attraction is generated in the inter-electrode gap G2 and the holding section 522 bends. As a result, the movable section 521 is displaced to the fixed substrate 51 side. It is possible to set the inter-reflective film gap G1 to a desired dimension.

4. Configuration of the Control Device

The control device 4 controls the overall operation of the colorimetric apparatus 1.

As the control device 4, for example, a general-purpose personal computer, a portable information terminal, a computer dedicated to colorimetry, and the like can be used.

The control device 4 includes, as shown in FIG. 12, a light-source control unit 41, a colorimetric-sensor control unit 42, and a calorimetric processing unit 43.

The light-source control unit 41 is connected to the light source device 2. The light-source control unit 41 outputs a predetermined control signal to the light source device 2 on the basis of, for example, a setting input of a user and causes the light source device 2 to emit white light having predetermined brightness.

The colorimetric-sensor control unit 42 is connected to the colorimetric sensor 3. The colorimetric-sensor control unit 42 sets wavelength of light, which the colorimetric-sensor control unit 42 causes the colorimetric sensor 3 to receive, on the basis of, for example, a setting input of the user, and outputs, to the colorimetric sensor 3, a control signal indicating that a received light amount of the light having the wavelength is detected. Consequently, the voltage control unit 32 of the colorimetric sensor 3 sets, on the basis of the control signal, an applied voltage to the electrostatic actuator 56 to transmit only the wavelength of the light desired by the user.

The colorimetric processing unit 43 analyzes the chromaticity of the test target X from the received light amount detected by the detecting unit 31.

5. Action and Effects of the Embodiment

The colorimetric apparatus 1 according to this embodiment includes an optical filter device 600 according to the first embodiment. As explained above, with the optical filter device 600, even if the movable substrate 52 and the base substrate 610 are fixed using the fixing member 7, the stress due to the difference between the coefficients of thermal expansion and the like less easily acts on the movable substrate 52 and the fixed substrate 51. Therefore, it is possible to suppress warping of the fixed reflective film 54 of the fixed substrate 51 and the movable reflective film 55 of the movable substrate 52. Therefore, it is possible to prevent a change in the optical characteristics of the variable wavelength interference filter 5 due to warping of the reflective films 54 and 55. In the optical filter device 600, since the air tightness of the inner space 650 is high and foreign matters such as water particles do not intrude into the inner space 650, it is possible to prevent a change in the optical characteristics of the variable wavelength interference filter 5 due to the foreign matters. Therefore, in the colorimetric sensor 3, it is possible to detect, with the detecting unit 31, light having target wavelength extracted at high resolution and detect an accurate light amount of light having desired target wavelength. Consequently, the colorimetric apparatus 1 can carry out an accurate color analysis of the test target X.

The detecting unit 31 is provided to be opposed to the base substrate 610. The detecting unit 31 and the outer side terminal sections 616 provided on the base outer side surface 613 of the base substrate 610 are connected to one circuit board 311. In other words, since the base substrate 610 of the optical filter device 600 is arranged on a light emission side, the base substrate 610 can be arranged close to the detecting unit 31 that detects light emitted from the optical filter device 600. Therefore, as explained above, it is possible to simplify a wiring structure and reduce the number of substrates by laying wires on the one circuit board 311.

The voltage control unit 32 may be arranged on the circuit board 311. In this case, it is possible to realize further simplification of the configuration.

Modifications

The invention is not limited to the embodiments explained above. Modifications, improvements, and the like within a range in which the object of the invention can be attained are included in the invention.

For example, in the first embodiment, the base substrate 610 and the lid 620 are joined in vacuum to manufacture the optical filter device 600 in which the inner space 650 is maintained in a vacuum state. However, the manufacturing of the optical filter device 600 is not limited to this. For example, hole sections for causing the inner space and the outside to communicate with each other may be formed in the lid and the base substrate. After the lid and the base substrate are joined under the atmospheric pressure, the inner space is evacuated of air to be changed to a vacuum state. The hole sections can be sealed by sealing members. Examples of the sealing members include metal balls. When the hole sections are sealed by the metal balls, it is desirable to fit the metal balls in the hole sections and then raise the temperature in the hole sections to weld the metal balls to the inner walls of the hole sections.

The variable wavelength interference filter 5 housed in the optical filter device 600 is not limited to the example explained in the embodiments. In the variable wavelength interference filter 5 of the type explained in the embodiments, the size of the inter-reflective film gap G1 can be changed using electrostatic attraction by applying voltage to the fixed electrode 561 and the movable electrode 562. Besides such a type, for example, as the actuator that changes the inter-reflective film gap G1, a dielectric actuator may be used in which a first dielectric coil is arranged instead of the fixed electrode 561 and a second dielectric coil or a permanent magnet is arranged instead of the movable electrode 562.

Further, a piezoelectric actuator may be used instead of the electrostatic actuator 56. In this case, for example, a lower electrode layer, a piezoelectric film, and an upper electrode layer are laminated and arranged in the holding section 522 and voltage applied between the lower electrode layer and the upper electrode layer are changed as an input value. Consequently, it is possible to expand and contract the piezoelectric film to bend the holding section 522.

The variable wavelength interference filter 5 is illustrated as the interference filter housed in the inner space 650. However, for example, the interference filter may be an interference filter in which the size of the inter-reflective film gap G1 is fixed. In this case, the holding section 522 for bending the movable section 521, the electrode arrangement groove 511 for providing the fixed electrode 561, and the like do not need to be formed by etching. The configuration of the interference filter can be simplified. Since the size of the inter-reflective film gap G1 is fixed, there is no problem in responsiveness and the inner space 650 does not need to be maintained vacuum. Therefore, it is possible to realize simplification of the configuration and improvement of manufacturing properties. However, even in this case, when the optical filter device 600 is used in, for example, a place where a temperature change is large, it is likely that the base side glass substrate 630 and the lid side glass substrate 640 receive stress and bend because of expansion of the air in the inner space 650. Therefore, even when such an interference filter is used, it is desirable to maintain the inner space 650 vacuum or in a decompressed state.

The lid 620 includes the lid joining section 624, the sidewall section 625, and the top surface section 626. The top surface section 626 is parallel to the base substrate 610. However, the shape of the lid 620 is not limited to this. The shape of the lid 620 may be any shape as long as the inner space 650 in which the variable wavelength interference filter 5 can be housed can be formed between the lid 620 and the base substrate 610. For example, the top surface section 626 may be formed in a curved surface shape. However, in this case, it is possible that manufacturing is complicated. This is because, for example, in order to maintain the air tightness of the inner space 650, it is necessary to form the lid side glass substrate 640 joined to the lid 620 in a curved surface shape to match the lid 620 and form only a portion for closing the light passing hole 621 in a plane shape to prevent refraction and the like from occurring. Therefore, as in the first embodiment, it is desirable to use the lid 620, the top surface section 626 of which is parallel to the base substrate 610.

In the example explained in the embodiments, the base side glass substrate 630 and the lid side glass substrate 640 are joined to the outer surface of the housing 601, i.e., the base outer side surface 613 of the base substrate 610 and the lid outer side surface 623 of the lid 620. However, the joining of the base side glass substrate 630 and the lid side glass substrate 640 is not limited to this. For example, the base side glass substrate 630 and the lid side glass substrate 640 may be joined to the inner space 650 side of the housing 601.

When a reflective filter that reflects light multiply interfered by the first reflective film and the second reflective film is housed in the inner space 650 as the interference filter, the light passing hole 611 and the base side glass substrate 630 do not have to be provided.

In this case, for example, a beam splitter may be provided to be opposed to the light passing hole 621 of the optical filter device 600 to separate incident light on the optical filter device 600 and emission light emitted from the optical filter device 600. Consequently, it is possible to cause the detecting unit to detect the separated emission light.

In the embodiments, the configuration is illustrated in which the inner side terminal sections 615 and the outer side terminal sections 616 are connected to, via the conductive member, the inside of the through-holes 614 provided in the base substrate 610. However, the connection of the inner side terminal sections 615 and the outer side terminal sections 616 is not limited to this. For example, bar-like terminals may be pressed into the through holes 614 of the base substrate 610 to connect the distal end portions of the terminals and the fixed electrode pad 563P, the movable electrode pad 564P, and the like.

In the embodiments, as the electrodes according to the embodiment of the invention provided in the variable wavelength interference filter 5, the fixed electrode 561 and the movable electrode 562 (and the electrode pads 563P and 564P connected to the electrodes 561 and 562) included in the electrostatic actuator are illustrated. However, the electrodes are not limited to this.

Other examples of the electrodes according to the embodiment of the invention include capacitance detection electrodes for measuring the size of the inter-reflective film gap G1 from a change in charge retention amounts of the fixed reflective film 54 and the movable reflective film 55 and charge removing electrodes for allowing charges retained in the fixed reflective film 54 and the movable reflective film 55 to escape and removing a Coulomb force between the substrates. In this case, extracting electrodes drawn out from the capacitance detecting electrodes, the charge removing electrodes, or the like are arranged on the first electric surface 514 and the second electric surface 524. Even when such a plurality of electrodes are arranged, by, for example, sticking the FPC 615A to the first electric surface 514, it is possible to easily carry out the wire connection without individually carrying out connection work for the electrodes in, for example, S12 of FIG. 5.

In the embodiments, the non-translucent member 515 is provided on the light incident surface of the fixed substrate 51. However, the non-translucent member 515 may be provided on the lid side glass substrate 640, which is the light transmitting substrate on the incident side.

In the embodiments, the optical filter device 600 is illustrated that causes light made incident from the lid 620 side to repeatedly interfere with the variable wavelength interference filter 5 and emits the light transmitted through the variable wavelength interference filter 5 from the base side glass substrate 630. However, for example, the light may be made incident from the base substrate 610 side. In this case, a non-translucent member functioning as an aperture may be provided on the movable substrate 52. Alternatively, the fixed substrate 51 on which the non-translucent member is provided may be fixed to the base substrate 610.

As the electronic apparatus according to the embodiment of the invention, the colorimetric apparatus 1 is illustrated in the sixth embodiment. Alternatively, the optical filter device, the optical module, and the electronic apparatus according to the embodiment of the invention can be used according to in various fields.

For example, the electronic apparatus can be used as a light-base system for detecting the presence of a specific substance. Examples of the system include a vehicle-mounted gas leak detector that detects specific gas at high sensitivity by adopting a spectrum measuring system in which the variable wavelength interference filter included in the optical filter device according to the embodiment of the invention is used and a gas detecting apparatus such as an optoacoustic rare gas detector for an expiration test.

An example of the gas detecting apparatus is explained below on the basis of the drawings.

Figure 13:
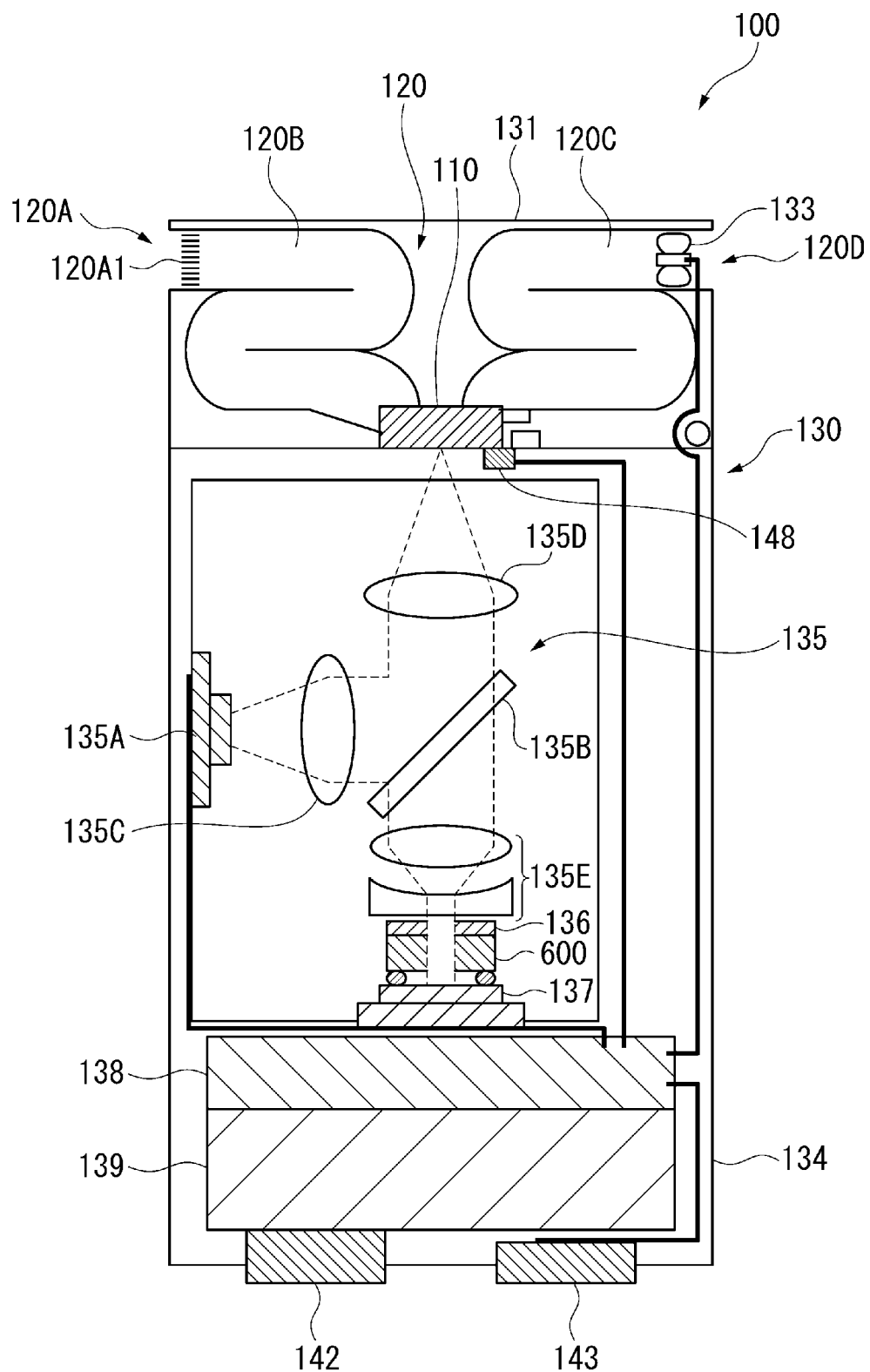
FIG. 13 is a schematic diagram showing a gas detecting apparatus including an optical filter device according to an embodiment.

FIG. 13 is a schematic diagram showing an example of the gas detecting apparatus including the variable wavelength interference filter.

Figure 14:
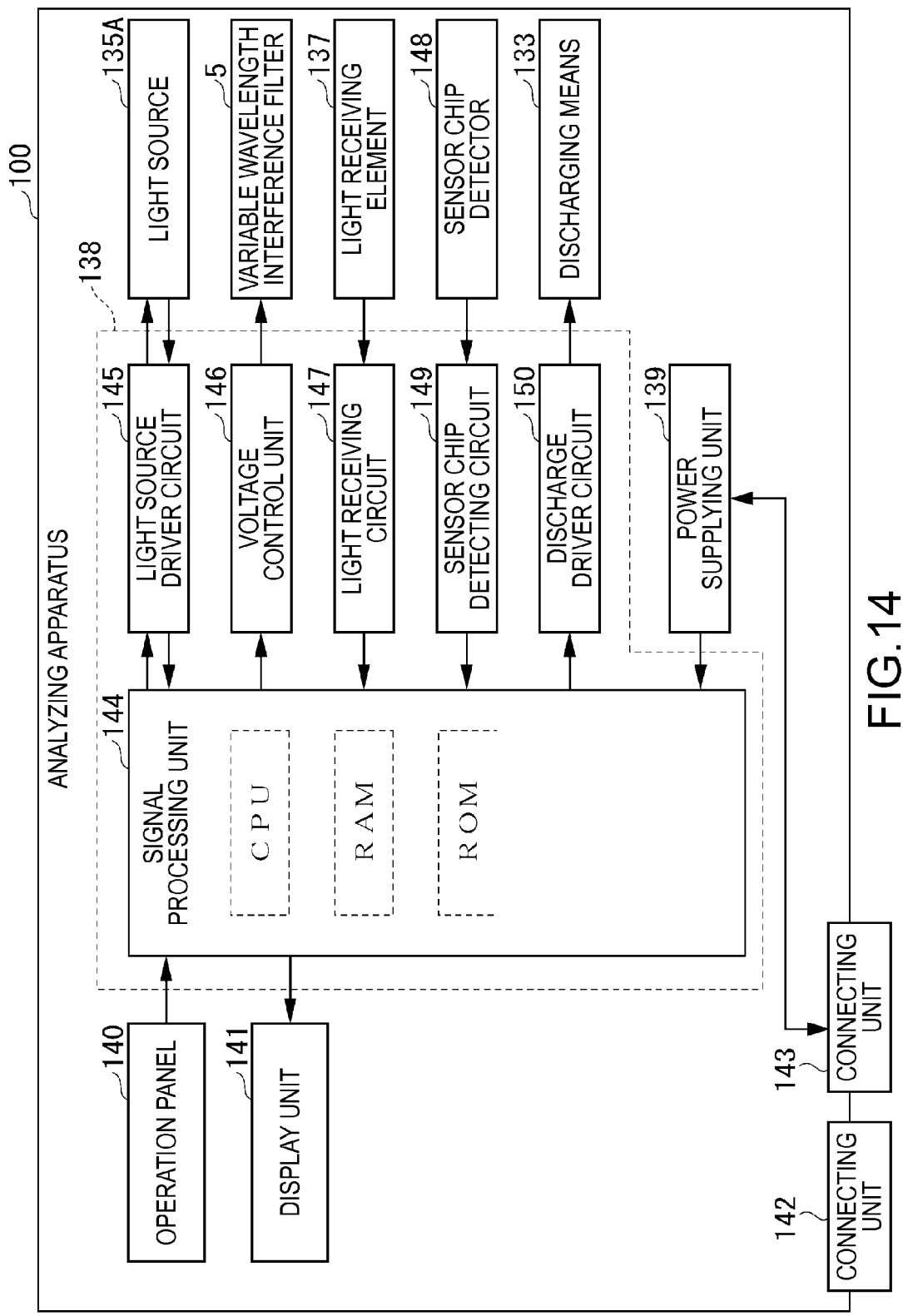
FIG. 14 is a block diagram showing the configuration of a control system of the gas detecting apparatus shown in FIG. 13.

FIG. 14 is a block diagram showing the configuration of a control system of the gas detecting apparatus shown in FIG. 13.

The gas detecting apparatus 100 includes, as shown in FIG. 13, a sensor chip 110, a channel 120 including a suction port 120A, a suction channel 120B, a discharge channel 120C, and a discharge port 120D, and a main body section 130.

The main body section 130 includes a sensor section cover 131 having an opening to which the channel 120 is detachably attachable, a discharging unit 133, a housing 134, an optical unit 135, a detecting device including a filter 136, the optical filter device 600, and a light receiving element 137 (a detecting section), a control section 138 configured to process a detected signal and control the detecting section, and a power supply unit 139 configured to supply electric power. The optical unit 135 includes a light source 135A configured to emit light, a beam splitter 135B configured to reflect the light made incident from the light source 135A to the sensor chip 110 side and transmit light made incident from the sensor chip 110 side to the light receiving element 137 side, a lens 135C, a lens 135D, and a lens 135E.

As shown in FIG. 14, an operation panel 140, a display unit 141, a connecting unit 142 for interface with the outside, and a power supply unit 139 are provided on the surface of the gas detecting apparatus 100. When the power supply unit 139 is a secondary battery, the gas detecting apparatus 100 may include a connecting unit 143 for charging.

The control section 138 of the gas detecting apparatus 100 includes, as shown in FIG. 14, a signal processing unit 144 including a CPU, a light source driver circuit 145 for controlling the light source 135A, a voltage control unit 146 for controlling the variable wavelength interference filter 5 of the optical filter device 600, a light receiving circuit 147 configured to receive a signal from the light receiving element 137, a sensor chip detector 148 configured to read a code of the sensor chip 110 and detect presence or absence of the sensor chip 110, a sensor chip detecting circuit 149 configured to receive a signal from the sensor chip detector 148, and a discharge drive circuit 150 configured to control the discharging unit 133.

The operation of the gas detecting apparatus 100 is explained below.

The sensor chip detector 148 is provided on the inside of the sensor section cover 131 in an upper part of the main body section 130. The sensor chip detector 148 detects presence or absence of the sensor chip 110. When the signal processing unit 144 detects a detection signal from the sensor chip detector 148, the signal processing unit 144 determines that the sensor chip 110 is mounted and emits, to the display unit 141, a display signal for causing the display unit 141 to display the effect that a detection operation can be carried out.

For example, the operation panel 140 is operated by a user and an instruction signal to start detection processing is output from the operation panel 140 to the signal processing unit 144. Then, first, the signal processing unit 144 outputs a signal for light source actuation to the light source driver circuit 145 and actuates the light source 135A. When the light source 135A is driven, a stable laser beam having single wavelength, which is linearly polarized light, is emitted from the light source 135A. A temperature sensor and a light amount sensor are incorporated in the light source 135A. Information of the sensors is output to the signal processing unit 144. When the signal processing unit 144 determines, on the basis of temperature and a light amount input from the light source 135A, that the light source 135A is stably operating, the signal processing unit 144 controls the discharge driver circuit 150 to actuate the discharging unit 133. Consequently, a gas sample containing a target substance (gas molecule) to be detected is guided from the suction port 120A to the suction channel 120B, the inside of the sensor chip 110, the discharge channel 120C, and the discharge port 120D. A dust removing filter 120A1 is provided in the suction port 120A. Relatively large powder dust, a part of water vapor, and the like are removed.

The sensor chip 110 is a sensor that incorporates a plurality of sets of metal nano-structures and makes use of localized surface Plasmon resonance. In the sensor chip 110, a reinforced electric field is formed among the metal nano-structures by a laser beam. When gas molecules enter the reinforced electric field, Raman scattering light and Rayleigh scattering light including information concerning molecule oscillation are generated.

The Rayleigh scattering light and the Raman scattering light are made incident on the filter 136 through the optical unit 135. The Rayleigh scattering light is separated by the filter 136. The Raman scattering light is made incident on the optical filter device 600. The signal processing unit 144 controls the voltage control unit 146 to adjust voltage applied to the variable wavelength interference filter 5 of the optical filter device 600. The signal processing unit 144 causes the variable wavelength interference filter 5 of the optical filter device 600 to split the Raman scattering light corresponding to the gas molecules to be detected. Thereafter, when the split light is received by the light receiving element 137, a light reception signal corresponding to a received light amount is output to the signal processing unit 144 via the light receiving circuit 147.

The signal processing unit 144 compares spectrum data of the Raman scattering light corresponding to the gas molecules to be detected obtained as explained above and data stored in a ROM, determines whether the gas molecules are target gas molecules, and identifies a substance. The signal processing unit 144 causes the display unit 141 to display information concerning an obtained result and outputs the information to the outside from the connecting unit 142.

In FIGS. 13 and 14, the gas detecting apparatus 100 is illustrated that splits the Raman scattering light using the variable wavelength interference filter 5 of the optical filter device 600 and performs gas detection from the split Raman scattering light. Alternatively, the gas detecting apparatus may be used as a gas detecting apparatus that identifies a gas type by detecting a light absorption degree peculiar to gas. In this case, a gas sensor that causes gas to flow into a sensor and detects light absorbed by the gas in incident light is used as the optical module according to the embodiment of the invention. A gas detecting apparatus that analyzes and distinguishes the gas caused to flow into the sensor by the gas sensor is the electronic apparatus according to the embodiment of the invention. Even with such a configuration, it is possible to detect components of gas using the variable wavelength interference filter.

A system for detecting the presence of a specific substance is not limited to the detection of gas explained above. As the system, substance component analyzing apparatuses such as a non-invasive measurement apparatus for saccharides by near infrared spectrum and a non-invasive measuring apparatus for information concerning foods, living bodies, minerals, and the like.

As an example of the substance component analyzing apparatus, a food analyzing apparatus is explained below.

Figure 15:
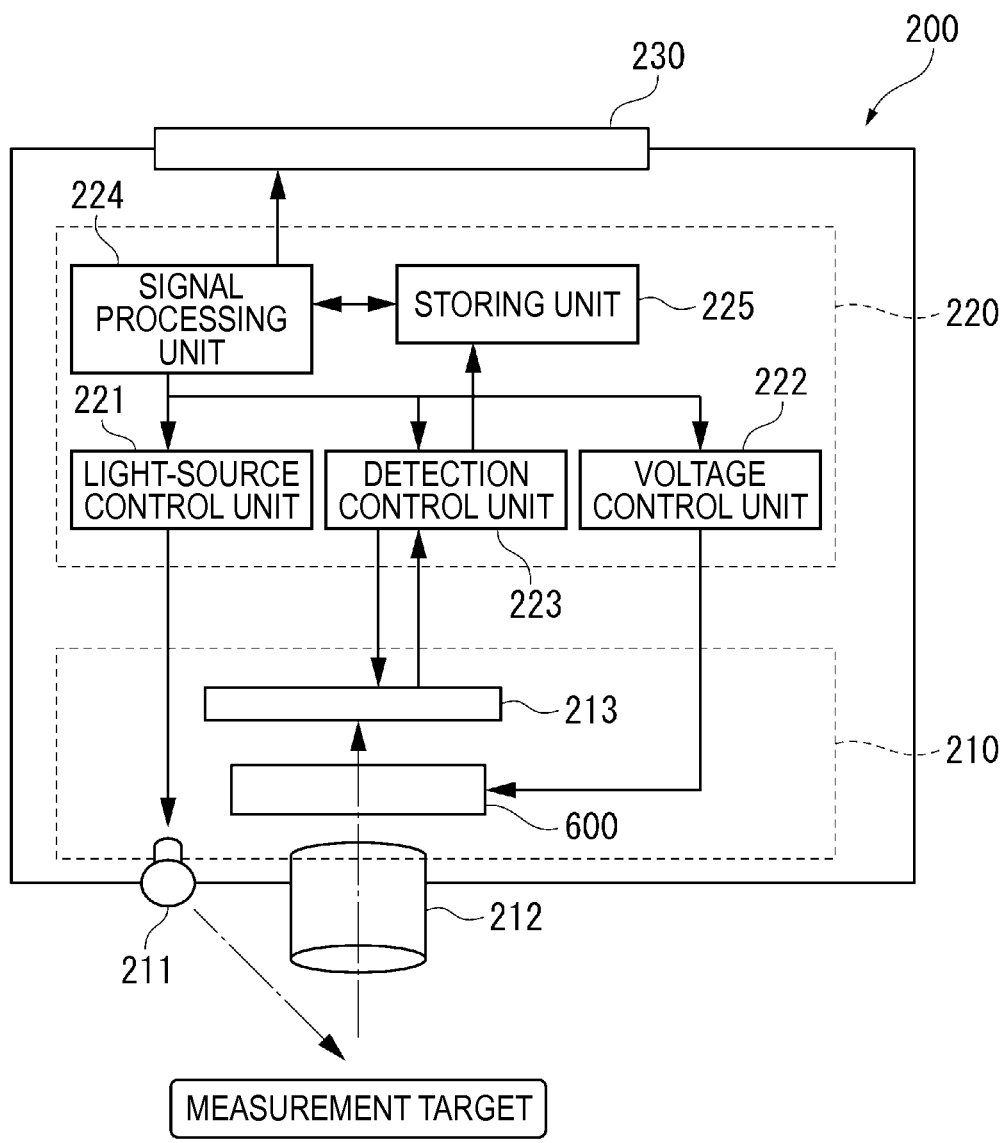
FIG. 15 is a diagram showing a schematic configuration of a food analyzing apparatus including the optical filter device according to the embodiment.

FIG. 15 is a diagram showing a schematic configuration of a food analyzing apparatus, which is an example of the electronic apparatus that makes use of the optical filter device 600.

The food analyzing apparatus 200 includes, as shown in FIG. 15, a detector 210 (an optical module), a control unit 220, and a display unit 230. The detector 210 includes a light source 211 configured to emit light, an image pickup lens 212 into which light from a measuring target is led, the optical filter device 600 configured to split the light led into the optical filter device 600 from the image pickup lens 212, and an image pickup unit 213 (a detecting unit) configured to detect the split light.

The control unit 220 includes a light-source control unit 221 configured to carry out lighting and extinguishing control for the light source 211 and brightness control during lighting, a voltage control unit 222 configured to control the variable wavelength interference filter 5 of the optical filter device 600, a detection control unit 223 configured to control the image pickup unit 213 and acquire a spectrum image picked up by the image pickup unit 213, a signal processing unit 224, and a storing unit 225.

In the food analyzing apparatus 200, when the system is driven, the light source 211 is controlled by the light-source control unit 221 and light is irradiated on a measurement target from the light source 211. The light reflected on the measurement target is made incident on the optical filter device 600 through the image pickup lens 212. Voltage capable of splitting light having a desired wavelength is applied to the variable wavelength interference filter 5 of the optical filter device 600 according to the control by the voltage control unit 222. An image of the split light is picked up by the image pickup unit 213 including a CCD camera. The picked-up image of the light is stored in the storing unit 225 as a spectrum image. The signal processing unit 224 controls the voltage control unit 222 to change a voltage value applied to the variable wavelength interference filter 5 and acquires spectrum images for respective wavelengths.

The signal processing unit 224 subjects pixel data in images accumulated in the storing unit 225 to arithmetic processing and calculates spectra in the pixels. In the storing unit 225, for example, information concerning components of foods corresponding to spectra is stored. The signal processing unit 224 analyzes data of the calculated spectra on the basis of the information concerning the foods stored in the storing unit 225 and calculates food components included in a test target food and contents of the food components. The signal processing unit 224 can calculate food calories, freshness, and the like from the obtained food components and contents. Further, the signal processing unit 224 can carry out, for example, extraction of a part where freshness falls in the test target food by analyzing a spectrum distribution in an image. Furthermore, the signal processing unit 224 can carry out detection of foreign matters and the like included in the food.

The signal processing unit 224 performs processing for causing the display unit 230 to display the information concerning the components and the contents of the components of the test target food, the calories, the freshness, and the like obtained as explained above.

In FIG. 15, the example of the food analyzing apparatus 200 is shown. However, the electronic apparatus can also be used as the non-invasive measuring apparatuses for the other kinds of information having substantially the same configuration. For example, the electronic apparatus can be used as a living body analyzing apparatus that performs analysis of living body components such as measurement and analysis of components of body fluid such as blood. For example, if the living body analyzing apparatus that measures components of body fluid such as blood is an apparatus that detects ethyl alcohol, the living body analyzing apparatus can be used as an apparatus for preventing driving under the influence of alcohol that detects a drunken state of a driver. The electronic apparatus can be used as an electron endoscope system including the living body analyzing apparatus.

Further, the electronic apparatus can be used as a mineral analyzing apparatus that carries out analysis of components of minerals.

Furthermore, the variable wavelength interference filter, the optical module, and the electronic apparatus according to the embodiment of the invention can be applied to apparatuses explained below.

For example, it is possible to transmit data with light having respective wavelengths by changing the intensities of the light having the respective wavelengths over time. In this case, it is possible to extract data transmitted by light having specific wavelength by splitting the light having the specific wavelength with the variable wavelength interference filter provided in the optical module and causing the light receiving unit to receive the light. It is also possible to carry out optical communication by processing the data of the light having the respective wavelengths using an electronic apparatus including such an optical module for data extraction.

The electronic apparatus can be applied to a spectrum camera, a spectrum analyzer, and the like that pick up a spectrum image by splitting light using the variable wavelength filter included in the optical filter device according to the embodiment of the invention. Examples of the spectrum camera include an infrared camera incorporating the variable wavelength interference filter.

Figure 16:
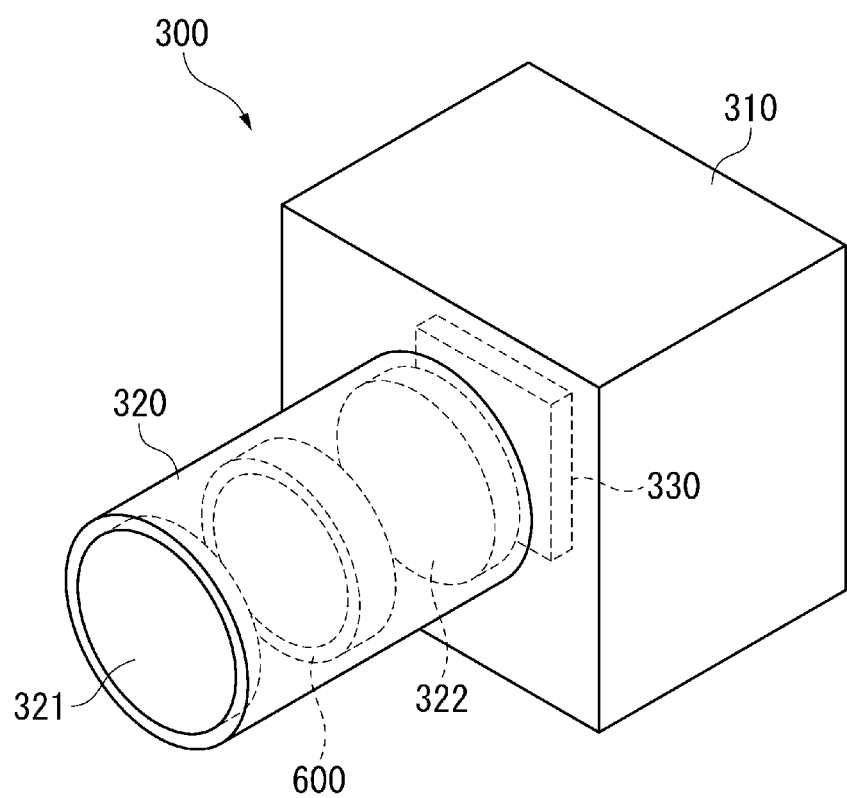
FIG. 16 is a schematic diagram showing a schematic configuration of a spectral camera including the optical filter device according to the embodiment.

FIG. 16 is a schematic diagram showing a schematic configuration of the spectrum camera. A spectrum camera 300 includes, as shown in FIG. 16, a camera body 310, an image pickup lens unit 320, and an image pickup unit 330 (a detecting unit).

The camera body 310 is a portion gripped and operated by a user.

The image pickup lens unit 320 is provided in the camera body 310 and guides incident image light to the image pickup unit 330. The image pickup lens unit 320 includes, as shown in FIG. 16, an objective lens 321, a focusing lens 322, and the optical filter device 600 provided between these lenses.

The image pickup unit 330 includes a light receiving element and picks up an image of the image light guided by the image pickup lens unit 320.

In the spectrum camera 300, it is possible to pick up a spectrum image of light having desired wavelength by transmitting light having wavelength, an image of which is picked up, using the variable wavelength interference filter 5 of the optical filter device 600.

Further, the variable wavelength interference filter included in the optical filter device according to the embodiment of the invention may be used as a band-pass filter. For example, the electronic apparatus can be used as an optical laser apparatus that splits, with the variable wavelength interference filter, only light in a narrow band centering on predetermined wavelength in light in a predetermined wavelength region emitted by a light emitting element and transmits the light.

The variable wavelength interference filter included in the optical filter device according to the embodiment of the invention may be used in a biometric identification apparatus. For example, the variable wavelength interference filter can be applied to authentication apparatuses for authenticating a blood vessel, a finger print, a retina, and an iris using light in a near infrared region and a visible region.

Further, the optical module and the electronic apparatus can be used as a density detecting apparatus. In this case, the density detecting apparatus splits, with the variable wavelength interference filter, infrared energy (infrared light) emitted from a substance, analyzes the infrared energy, and measures a subject density in a sample.

As explained above, the optical filter device and the electronic apparatus according to the embodiment of the invention can be applied to any apparatus that splits/filters predetermine light from incident light. As explained above, one optical filter device according to the embodiment of the invention can split light having a plurality of wavelengths. Therefore, it is possible to accurately carry out measurement of spectra of a plurality of wavelengths and detection of a plurality of components. Therefore, compared with the apparatus in the past that extracts desired wavelength using a plurality of devices, it is possible to facilitate a reduction in the sizes of the optical module and the electronic apparatus and suitably use the optical module and the electronic apparatus as portable and vehicle-mounted optical devices.

In the explanation of the examples of the colorimetric apparatus 1, the gas detecting apparatus 100, the food analyzing apparatus 200, and the spectrum camera 300, the optical filter device 600 according to the first embodiment is applied. However, the optical filter device is not limited to this. It goes without saying that the optical filter devices according to the other embodiments and the other optical filter devices according to the embodiment of the invention can also be applied to the colorimetric apparatus 1 and the like.

In the third embodiment, the fixing members 7 are arranged in the substrate recesses 527. However, the invention is not limited to such a form. For example, the substrate recesses 527 may be formed in a groove shape like the base recesses 618. On the other hand, the fixing members 7 may be arranged on the inside of the base recesses 618 as in the substrate recesses 527.

In the first embodiment, the movable substrate 52 and the base substrate 610 are fixed in one place by the fixing member 7 arranged at one point. The fixing by the fixing member at one point as in the first embodiment is included in the fixing in one place. However, in the invention, the fixing in one place is not limited to such a form.

Figure 17:
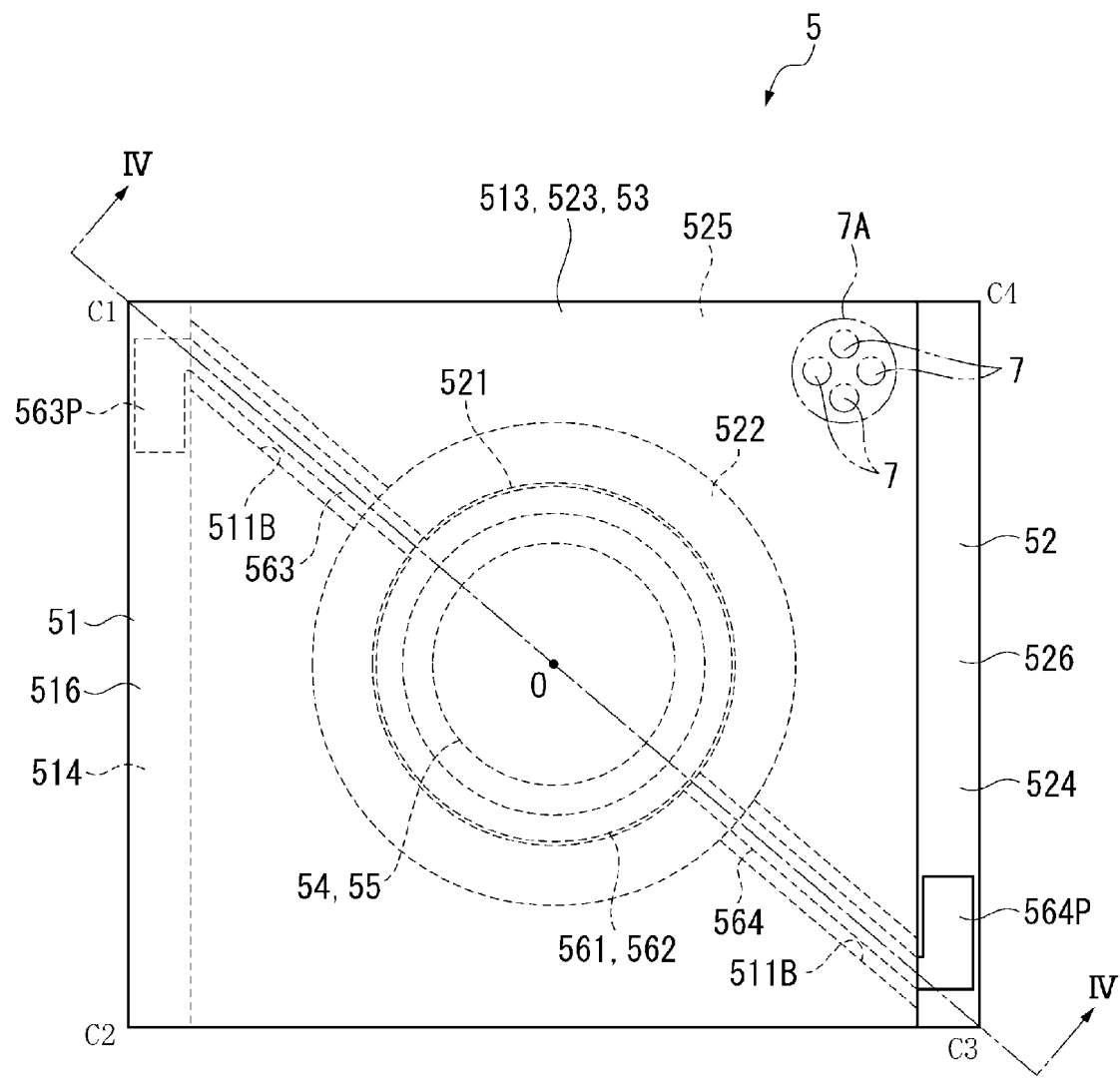
FIG. 17 is a plan view showing a schematic configuration of an interference filter housed in the optical filter device and is a diagram for explaining a positional relation between the interference filter and a fixing member.

For example, the fixing by the arrangement of the fixing members 7 shown in FIG. 17 is also included in the fixing in one place. FIG. 17 is a plan view showing a schematic configuration of the variable wavelength interference filter 5. The fixing members 7 arranged at a plurality of points are shown in FIG. 17. The fixing members 7 at the plurality of points are not dispersedly arranged from one another. As shown in FIG. 17, the fixing members 7 are concentratedly arranged in a region 7A closer to the vertex C4 than the movable reflective film 55. A place in which the fixing members 7 at the plurality of points are concentratedly arranged like the region 7A is also one place.

When the second substrate and the base substrate are fixed in one place where the fixing members at the plurality of points are concentratedly arranged, the stress due to the difference between the coefficients of thermal expansion and the contraction stress during the adhesive hardening less easily act on the second substrate and the first substrate. As a result, in the optical filter device, it is possible to suppress warping of the second reflective film and the first reflective film.

In the examples explained in the embodiments, the optical filter device includes the lid. However, the form of the optical filter device is not limited to this form. The optical filter device does not have to include the lid. The interference filter may be fixed to the base substrate in the predetermined place.

The specific structure in carrying out the invention can be changed as appropriate to other structures and the like in a range in which the object of the invention can be attained.

The entire disclosure of Japanese Patent Application No. 2012-029864 filed Feb. 14, 2012 is expressly incorporated by reference herein.

What is claimed is:

1. An optical filter device comprising:
an interference filter including a first substrate, a second substrate opposing the first substrate and joined to the first substrate, a first reflective film provided on the first substrate, and a second reflective film provided on the second substrate and opposing the first reflective film across an inter-reflective film gap; and
a housing supporting the interference filter, wherein
the housing includes a base substrate on which the interference filter is arranged,
an adhesive member fixing the second substrate to the base substrate is arranged between the second substrate and the base substrate, and
the second substrate is fixed to the base substrate by the adhesive member in one place excluding a region where the second reflective film is provided in a plan view such that the interference filter is supported in a cantilevered manner relative to the base substrate.

2. The optical filter device according to claim 1, wherein, the second substrate is fixed to an outer peripheral portion of a surface opposed to the base substrate in the plan view.

3. The optical filter device according to claim 1, wherein, the second substrate is fixed to a corner portion of a surface opposed to the base substrate in the plan view.

4. An optical filter device comprising:
an interference filter including a first substrate, a second substrate opposing the first substrate and joined to the first substrate, a first reflective film provided on the first substrate, and a second reflective film provided on the second substrate and opposing the first reflective film across an inter-reflective film gap; and
a housing supporting the interference filter, wherein
the housing includes a base substrate on which the interference filter is arranged,
the second substrate includes a non-joining section not joined to the first substrate, and
an adhesive member that fixes the second substrate to the base substrate is arranged between the non-joining section and the base substrate,
wherein the second substrate is fixed to the base substrate by the adhesive member in one place of the non-joining section such that the interference filter is supported in a cantilevered manner relative to the base substrate.

5. The optical filter device according to claim 4, wherein, the non-joining section is a projecting section where the second substrate projects further to an outer side than the first substrate in a plan view.

6. The optical filter device according to claim 5, further comprising:
an actuator configured to bend the second substrate by applying voltage and change a gap distance of the inter-reflective film gap, wherein
the actuator includes a first electrode provided on the first substrate and a second electrode provided on the second substrate and opposing the first electrode, and
a second terminal extracting section connected to the second electrode is formed on the projecting section.

7. The optical filter device according to claim 1, wherein a substrate recess is formed in a position corresponding to the fixing member on a surface of the second substrate opposing the base substrate.

8. The optical filter device according to claim 1, wherein a base recess is formed in a position corresponding to the fixing member on a surface of the base substrate opposing the second substrate.

9. The optical filter device according to claim 1, further comprising a lid joined to the base substrate and configured to form an inner space in which the interference filter is housed, between the lid and the base substrate.

10. A manufacturing method for an optical filter device comprising:
forming a first reflective film on a first substrate;
forming a second reflective film on a second substrate;
joining the first substrate and the second substrate such that the first reflective film and the second reflective film oppose each other across an inter-reflective film gap to form an interference filter;
arranging an adhesive member on a base substrate, wherein the second substrate is fixed to the base substrate with the adhesive member in one place excluding a region where the second reflective film is formed such that the second substrate is supported in a cantilevered manner relative to the base substrate; and
joining a lid to the base substrate, the lid configured to form an inner space in which the interference filter is housed between the lid and the base substrate.

11. A manufacturing method for an optical filter device comprising:
forming a first reflective film on a first substrate;
forming a second reflective film on a second substrate;
joining the first substrate and the second substrate such that the first reflective film and the second reflective film oppose each other across an inter-reflective film gap to form an interference filter;
arranging an adhesive member on a base substrate, wherein the second substrate is fixed to the base substrate with the adhesive member such that the second substrate is supported in a cantilevered manner relative to the base substrate; and
joining a lid to the base substrate, the lid configured to form an inner space in which the interference filter is housed between the lid and the base substrate, wherein
in the joining of the first substrate and the second substrate and forming of the interference filter, when the first substrate and the second substrate are joined, a non-joining section not joined to the first substrate is formed on the second substrate, and
the second substrate is fixed to the non-joining section.

12. An optical filter device comprising:
an interference filter, the interference filter including a first substrate, a second substrate that is opposing to the first substrate, a first reflector that is disposed between the first substrate and the second substrate, and a second reflector that is disposed between the first reflector and the second substrate, wherein the first reflector is opposed to the second reflector, and a gap exists between the first reflector and the second reflector;
a housing that houses the interference filter; and
an adhesive member that is disposed between the second substrate and the housing to support the second substrate in a cantilevered manner relative to the base substrate,
wherein, when viewing the optical filter device in a direction toward the second reflector from the first reflector, the fixing member is disposed in a single location that excludes a region where the second reflector is disposed, and
wherein the housing includes a base, and the adhesive member fixes the second substrate to the base.

13. The optical filter device of claim 1, wherein the base substrate is separate and apart from the first and second substrates on which the interference filter is arranged.

14. The optical filter device of claim 4, wherein the base substrate is separate and apart from the first and second substrates on which the interference filter is arranged.

15. The method of claim 10, wherein the base substrate is separate and apart from the first and second substrates.

16. The method of claim 11, wherein the base substrate is separate and apart from the first and second substrates.

17. The optical filter device of claim 1, wherein the adhesive member is located exterior to the interference filter, and fixes the second substrate directly to the base substrate.

18. The optical filter device of claim 4, wherein the adhesive member is located exterior to the interference filter, fixes the second substrate directly to the base substrate.

19. The optical filter device of claim 12, wherein the adhesive member is located exterior to the interference filter, fixes the second substrate directly to the base.

* * * * *